(12) United States Patent
McErlean et al.

(10) Patent No.: US 8,539,742 B2
(45) Date of Patent: Sep. 24, 2013

(54) METHOD FOR EMPTYING PHARMACEUTICAL CONTAINER

(75) Inventors: James G. McErlean, Uniondale, PA (US); E. Christian Hess, Flanders, NJ (US); Chih-Jen Leu, East Brunswick, NJ (US); Mark A. Detri, Lafayette, NJ (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 0 days.

(21) Appl. No.: 13/401,451

(22) Filed: Feb. 21, 2012

(65) Prior Publication Data

US 2013/0000260 A1 Jan. 3, 2013

Related U.S. Application Data

(60) Division of application No. 12/463,776, filed on May 11, 2009, now Pat. No. 8,117,809, which is a division of application No. 10/634,992, filed on Aug. 6, 2003, now Pat. No. 7,530,211, which is a continuation-in-part of application No. 10/215,249, filed on Aug. 9, 2002, now Pat. No. 6,892,512.

(60) Provisional application No. 60/401,340, filed on Aug. 7, 2002.

(51) Int. Cl.
*B65B 57/02* (2006.01)

(52) U.S. Cl.
USPC .............. 53/505; 53/75; 53/67; 414/403

(58) Field of Classification Search
USPC .............. 53/492, 505, 67, 75; 414/403, 408, 414/411, 412, 810
See application file for complete search history.

(56) References Cited

U.S. PATENT DOCUMENTS

| | | | | |
|---|---|---|---|---|
| 4,988,255 | A * | 1/1991 | Hoffman | 414/412 |
| 5,318,420 | A * | 6/1994 | Blaimschein | 425/174.2 |
| 5,423,216 | A * | 6/1995 | Kitamura et al. | 73/433 |
| 5,611,378 | A * | 3/1997 | Brazell | 144/135.2 |
| 5,720,154 | A * | 2/1998 | Lasher et al. | 53/411 |
| 5,771,657 | A * | 6/1998 | Lasher et al. | 53/55 |
| 6,494,017 | B1 * | 12/2002 | McGrath et al. | 53/53 |
| 6,580,968 | B1 * | 6/2003 | Yuyama et al. | 700/241 |
| 6,644,504 | B2 * | 11/2003 | Yuyama et al. | 221/265 |
| 6,715,266 | B2 * | 4/2004 | Browning | 53/492 |
| 6,892,512 | B2 * | 5/2005 | Rice et al. | 53/445 |
| 2004/0059463 | A1 * | 3/2004 | Coughlin | 700/229 |

FOREIGN PATENT DOCUMENTS

GB 2068829 * 8/1981

* cited by examiner

*Primary Examiner* — Hemant M Desai
(74) *Attorney, Agent, or Firm* — Husch Blackwell LLP

(57) ABSTRACT

An automated system and method for emptying the contents of pharmaceutical containers. In an embodiment, a gripper unit receives and holds a pharmaceutical container. A cutter cuts the pharmaceutical container, and a rotating unit, operable with the gripper, rotates at least a portion of the gripper unit to empty the contents of the pharmaceutical container.

19 Claims, 27 Drawing Sheets

METHOD FOR EMPTYING
PHARMACEUTICAL CONTAINER

RELATED APPLICATIONS

This application is a divisional application of U.S. application Ser. No. 12/463,776, filed May 11, 2009, now U.S. Pat. No. 8,117,809, which is a divisional application of U.S. application Ser. No. 10/634,992, filed Aug. 6, 2003, now U.S. Pat. No. 7,530,211, which claims priority to, and is a continuation-in-part of U.S. application Ser. No. 10/215,249, filed Aug. 9, 2002, now U.S. Pat. No. 6,892,512 which claims priority from U.S. provisional application Ser. No. 60/401,340 filed Aug. 7, 2002, all of the above applications are incorporated herein by reference in their entirety.

FIELD OF THE INVENTION

The present invention generally relates to systems and methods for emptying the contents of pharmaceutical containers, including medications, into a container to facilitate the automated and/or manual dispensing of pharmaceuticals. The present invention also generally relates to systems and methods for automatically combining pharmaceuticals and/or medications for later dispensing and/or packaging of pharmaceuticals, medications, prescriptions and/or prescription orders, automatically and/or manually. The present invention may be used for mail order pharmacies, wholesalers and/or central fill dealers for subsequent distribution or sale including a retailer.

BACKGROUND OF THE INVENTION

In mail service pharmacies and large retail pharmacies, prescription drugs are dispensed in a high volume. For such services, it is known to use an automatic pill dispensing system to carry out the dispensing of the prescription drugs automatically at a rapid rate and to label pill containers which can then be provided to the patient for whom the prescriptions were written.

A known automatic pill dispensing system is described in U.S. Pat. No. 5,771,657 issued to Lasher et al., which is incorporated herein by reference. In the patent, as shown in the schematic illustration of FIG. 1A, orders (e.g., orders to fill prescriptions) are received by a host computer 9 which forwards the orders to a distributed computer system including a central computer called Pharmacy Automation Controller 10 (PAC). PAC 10 maintains an order file of the information about each prescription to be filled in an order including all of the information needed to fill each prescription, and prepares a prescription label for each prescription and the information to print literature to go in a shipping container with the prescription or prescriptions. PAC updates the order file to maintain a record of the current status of each prescription being filled as it progresses through the automated system.

PAC 10 controls a set of Print, Apply and Load (PAL) stations 14 which print prescription bottle labels, apply the prescriptions to prescription bottles, and load the labeled bottles onto bottle carriers that preferably receive the bottles in scheduled locations. PAC 10 also controls a carrier conveyer system 21 that carries the bottle carriers to different parts of the system, and one or more automatic drug dispensing machines 23 that dispense tablets and/or capsules into the prescription bottles in the bottle carriers as they are carried by the conveyer system 21. PAC 10 also controls bottle cappers 25 that apply caps to the bottles, and one or more OCP stations 29 that unload bottles from the carriers and place them in the shipping containers corresponding to the patient orders.

PAC 10 also controls literature printers 31 which print literature for each prescription order and enclose the literature for each prescription order in an envelope, print a bar code that shows through a window in the envelope identifying the prescription order, and then place each envelope on a literature conveyer 34 which carries the envelope from the literature printers 31 to the OCP stations 29.

The conveyer system 21 carries the bottles in the carriers from the PAL stations through the automatic drug dispensing machines 23 to the bottle cappers 25 and then from the bottle cappers to the OCP stations 29. The conveyer system 21 also carries the empty carriers back to the PAL stations 14. From the bottle cappers 25, the conveyers 56 feed the carriers onto an endless conveyer loop 71 which will transport the four carriers of a rank to one of six OCP stations 29.

The OCP stations each also have a literature dispensing mechanism, which inserts printed literature into each shipping container with the filled and capped prescription bottles.

As shown in FIG. 1B, bottles to be automatically filled with the prescription drugs are introduced to the automated system by hoppers 37, which receive the bottles in bulk form and automatically feed the bottles to unscramblers 39. One of the hoppers 37 and one of the unscramblers 39 will be for large bottles (e.g., 160 cc), and the remaining hoppers and unscramblers will be for small bottles (e.g., 110 cc). The small bottle size can preferably accommodate a majority of the automatically filled prescriptions. In the unscramblers, the bottles are singulated and oriented so that the bottle opening first faces downward. The bottles are then righted and directed to PAL stations 14 on bottle conveyers 41 and 43, one for large bottles and one for small bottles.

As shown in FIG. 1B, the conveyers 45, under control by PAC, carry the bottle carriers from the four PAL stations 14 to carrier buffers at the entrances of the four automatic drug dispensing machines 23 in which the tablets or capsules of the prescriptions are automatically dispensed into the prescription bottles under the control of PAC 10. Because of the organization provided by the carriers, the bottles are arranged into four columns approaching each automatic dispensing machine 23. Since there are four automatic dispensing machines 23, 16 parallel prescription bottle columns approach the dispensing machines. In the specific embodiment of the invention, the four automatic drug dispensing machines each have 384 drug dispensers arranged four columns wide and 96 rows deep to provide a total of 1,536 pill dispensers. The automatic drug dispensing machines are similar to those described in the U.S. Pat. No. 5,660,305, which is hereby incorporated by reference. Each dispensing lane is divided into 32 buffer assemblies each containing twelve drug dispensers oriented six on each side of a conveyer within the dispensing machine.

The carrier will be released by the PAL station 14 onto a conveyer 45 which carries the carrier loaded with the labeled empty prescription bottles to an automatic dispensing machine 23, of which there are four, one for each PAL station 14. When a carrier moves out of the last row position in a dispensing machine, all of the prescription bottles in that bottle carrier should be filled and a conveyer 56 transports the prescription bottles now filled with the prescriptions to a bottle capper 25.

The bottle quality assurance area 109 has several stations at which pharmacists will scan the bar code on the bottles and visually inspect the contents of the bottles. The scan of the bottle bar code will bring up a display on the pharmacist's terminal which includes all the information regarding the particular prescription and order including the drug name, and instructions which identify the reason for the verification. All of the bottles that pass this inspection are inserted by the pharmacist on a bottle stream conveyer 111 to send the inspected bottles to the BSP station 112. The conveyer 108 leads to a star wheel diverter mechanism 114 which under the control of a controller for the BSP station deposits the bottle in a bottle stream conveyer 116 leading to the bottle quality assurance area 109 or into a bottle stream conveyer 118 leading to BSP station 112.

If the literature pack is on the conveyer 34, but because of failure of the bar code reader (not shown) or the literature sorting mechanism, does not get diverted at station 112, the conveyer 34 will carry the literature package to the package quality assurance area where it can be manually added to the package. If, because of a malfunction, a literature envelope is not deflected by a deflector (not shown), because of, for example, an improper bar code on the envelope, the envelope will continue on the conveyer 34 to the end of the conveyer and be dumped into a receptacle at the package quality assurance station 96. If the bag does not contain a literature pack, then the bag is diverted into a tote (not shown) which will then be transported by a conveyer 101 to the package quality assurance station 96 where the shipping container will be assembled with the literature pack manually 137. FIG. 2 shows another known dispensing system as described in U.S. patent application Ser. No. 10/215,249, which is incorporated herein by reference. In particular, FIG. 2 shows a system 250 that can include a storage device for packages 203, dispenser for the packages 205, storage device for bottles filled with counted pills 209, dispenser for the bottled with counted pills 207, storage device for patient specific literatures 211, dispenser for the patient specific literatures 213, consolidation station 215, and host computer 201. System 250 can be referred to as a automated labeling and packaging system (ALPS).

The system shown in FIG. 2 can also include one or more local computers (not shown). For instance, each of the components (e.g., 203, 205, 209, 207, 211 and 213) can be connected to one or more local computers. The local computers in turn are connected to host computer 201. In this way, host computer 201 and local computers are configured to control the various components of the present invention.

A local computer can also function with a standard Programmable Logic Controller (PLC). A PLC typically includes an I/O card to turn on/off a device. Accordingly, when a component is to be controlled by turning it on/off, a PLC can be used. When a large quantity of data is to be exchanged, a local computer can be used.

Host computer 201 can receive a request to fill an order, optionally in combination with the local computer(s) and/or the various components. In response, host computer 201 creates an order number and determines whether the order contains an order that requires bottles to be filled by counting individual tablets and whether the order contains an order that requires packages from the storage device for bottles 209.

The storage device for packages 203 stores packages that contain pharmaceutical products. For example, one set of packages may contain a predetermined number of tablets (e.g., 500 tablets) of a certain drug (e.g., Allegra). Another set of example packages may include liquid pharmaceutical products. The packages can be made by original producers of drugs (e.g., Hoechst Marion Roussel). The packages can also be bulk bottles that are filled by any one of many automated (e.g., the ADDS) or manual methods known in the art. These packages can then be shelved so that their locations can be automatically identified. In turn, the dispenser for the packages 205 is configured to automatically identify the location of any package with a certain type of drug, dosage and/or quantity and configured to pick one or more packages from the identified location. In other words, a package contains a pharmaceutical product without having been pre-designated for any specific order when the package was created.

In operation, the command to locate and pick one or more packages is received from host computer 201. The dispenser for packages can also be connected to its own local computer to perform the necessary functions to locate and pick one or more packages in accordance with the command from host computer 201. It should be noted that the packages stored in the storage device for packages 203 are not designated for any specific patient. In other words, any package can be picked to fill an order of a patient as long as the type of drug, dosage and/or quantity are matched with the order.

FIG. 2 can also include a standard sensor or a standard counter to indicate when a specific type of package is out of stock in the storage device for packages 203. These sensors or counters can be present at each location (or a substantial number of them). The signals from the sensors or counters can be communicated to, for example, the host computer 201 via the local computer. In turn, the host computer 201 can notify an operator or system to replenish the specific packages and/or stop the process of filling orders that require the specific type of package that are out of stock in the storage device for packages 203. In addition, or optionally, host computer 201 can send a query to the storage device for packages 203 regarding whether a certain number of certain packages are available to be dispensed. In response, the storage device for packages 203, or in combination with its local computer, can send a response based on information from the sensors and/or counters. Alternatively, sensors may be placed on the robot arm or picking device to provide the similar functionality. In yet another alternative, sensors are not utilized and the system keeps logical control by knowing how many packages have been placed in a channel and how many packages have been removed from the channel.

The dispenser for bottles 207 is configured to receive bottles that contain specific number (e.g., 1-500 or more) of pills for a specific order. For example, one bottle may include 350 tablets of one type of drug for patient A, while another bottle may include 600 tablets of another type of drug for patient B. The bottles can be filled by any automatic dispensing mechanisms known in the art (e.g., the system shown in U.S. Pat. No. 5,771,657). Bottles can also be manually filled (by, e.g., a pharmacist).

If an automatic dispensing system is used, host computer 201 sends commands to fill bottles with certain number of pills for a certain type of drug. Once they are filled, the bottles are stored in the storage device for bottles 209. In a similar fashion, in a manual system, the dispensing person would receive an instruction to count certain number of tablets for a certain type of drug. The person fills bottles according to the instructions and forwards the bottles to the storage device for bottles 209.

Once the storage device for bottles 209 receives all the bottles necessary to fill an order, the storage device for bottles 209 or in connection with its local computer sends a message to the host computer 201 indicating that the bottle portion of the order has been filled. For example, an order to fill an order may require 1450 pills of a certain type of drug. In this example, the storage device for packages 203 may already have two packages each with 500 pills of the drug. If so, one bottle with 450 pills of the drug is necessary to fill the bottle portion of the order. (If one bottle cannot receive all 450 pills then more than one bottle would become necessary to provide the 450 pills).

The storage device for literature packs 211 contains literatures to be packaged with specific orders. For example, a set of literature packs for one order may include information relating to each of the prescribed drugs, how often each drug must be taken, billing information, special instructions from the prescribing doctor, insurance information, refilling information and/or general information, for example health or notification of other services. The set of literature packs is then packaged per order and collected in the storage device for literature packs 211. Once the necessary literature packs are created, the storage device for literature packs 211, or in combination with its local computer, can notify the host computer 201 that the literature pack has been printed.

Upon receiving various information from the storage device for packages 203, storage device for bottles 209 and storage device for literature packs 211, host computer 201 then sends instructions to the dispenser for the packages 205, dispenser for bottles 207 and dispenser for literature packs 213, or to their local computers, to dispense necessary bottle(s), package(s) and literature pack(s) to fill one or more orders. The dispensed bottle(s), package(s) and literature pack(s) are then consolidated by the consolidation station 215 and then sent, distributed or mailed out directly or indirectly to patients associated with the orders.

FIG. 3 shows yet another known system as disclosed in U.S. Pat. No. 5,208,762 to Charhut et al., which is incorporated herein by reference. As illustrated in FIG. 3, a system 310 is provided for dispensing prescriptions. The system 310 includes three lines 312, 314 and 316 of machines that can automatically fill, label, cap, and sort vials 318 in accordance with a patient's prescription order under the control of an appropriate control system.

For ease of understanding, only one of lines 312, 314, and 316 will be described in detail. However, with the exception of vial size, the description is applicable to each of lines 312, 314, and 316. Therefore, reference numerals identifying items in the drawings which have counterparts associated with each line will be used generically in this description, but in the drawings will carry additional designations such as a, b, and c to identify those items corresponding to the particular lines.

The first machine position at each line of the system is a vial unscrambler 320. In such a machine, vials of one size are dumped into a hopper 322 in bulk form.

The unscrambler 320 orients the vials upright in a separator 323 and spaces them on a conveyor 324 ready to feed into a vial filler 326. The unscrambler 320 can also be equipped to shoot a blast of air into the vial, cleaning debris that might be present.

From the unscrambler 320, a vial will travel via the conveyor 324 to the vial filler 326 (also referred to as the filler). The vial filler 326 preferably comprises a modified Automatic Tablet Control (ATC) machine. The ATC machine is capable of holding up to about 480 different oral, solid medications. Such medications are held in canisters calibrated specifically for those drugs. There can be one or more ATC machines per line depending on drug mix and drug volume required by the institution in which the system 310 is installed.

The conveyor 324 brings the vial under a filling position of the filler 326 and a signal from the controller system activates the appropriate drug canister, as required. More than one canister can be assigned to a specific drug and can dispense doses simultaneously. The drug doses are counted into the vial until filling is complete.

After filling, the vial is labeled by a label machine 328 (also referred to as the labeler). The labeler 328 can be located downstream of the vial filler 326 as shown or it can preferably be located under the vial filler 326 to label vials during or immediately following filling. A signal from the control system is sent to the label machine 328 at the same time the vial is being filled. The label machine print human readable information, as well as bar code information on demand. The label information is kept in a data base and contains drug description, as well as any warning statements.

After the label is printed, a reader can be provided associated with the labeler 328, to verify the contents of the label by reading the printed bar code. Once a vial is filled and labeled, it travels down the conveyor 324 to a capping machine 330 (also referred to as the capper). The capping machine 330 grasps the vial and preferably applies a child-resistant cap 331 to the vial.

Just after the capper 330, each line includes a bar code reader 336 and a wrap belt 339 disposed on opposite sides of the conveyor 324. The wrap belt 339 serves to spin a vial around so that the bar code thereon can be read by the reader 336. The bar code reader 336 verifies the legibility of the bar code on the label and confirms the prescription number to the control system.

After the vial is capped, a sensor associated therewith verifies that the cap has been properly applied. The capper 330 preferably includes a reservoir 333 that is sufficiently large to store one full shift's supply of caps.

Once a vial has been capped and the contents are verified by the capper sensor 336, it proceeds to an accumulator or accumulation station 332 positioned at the end of its respective conveyor 324. The accumulation station 332 serves two functions: sorting and ejecting. Vials are ejected when they have an improper drug count, unreadable labels, or improperly seated caps. A signal sent by the filler 326, labeler 328, or capper 330 causes a defective vial to be ejected into a reject bin 335 by a blast of pneumatic air gun 334 if any of the situations is detected. When a vial is ejected, the control system places a refill request with the filler 326 on a priority basis so that another attempt is made to complete the prescription order.

A circulating conveyor 342 (also referred to as a sorting conveyor) carries circulating bins 340 along a path that brings each of the bins under an accumulator 332 once per rotation. The bins 340 are bar coded and the control system assigns at least one circulating bin 340 per patient. If a particular patient has more vials than a single bin can hold, a second or third bin will also be assigned. A bin 340 will circulate on the conveyor 342 until a patient's total order has been collected. The bar code on the bin 340 will be read by bar code reader 363 prior to travel under the accumulators 332 and a signal will correctly time an accumulator 332 to discharge a specific patient's vial into the bin 340.

All properly bottled vials are assigned to a location on the accumulator 332 where they await a circulating bin 340 in which they are to be placed. These locations are also referred to as the staging output area. The accumulator 332 preferably has up to twenty locations for temporary vial storage.

The accumulators 332 are positioned above the conveyor 342 so that the vials awaiting on an accumulator can be placed into a passing bin 340. To this end, each accumulator 332 has associated therewith a pneumatic gripper 337 on a rodless cylinder for placing upon command, a vial into an accumulator position.

One or more of the bins is assigned to a patient by the control system. As the assigned circulating bin(s) 340 move(s) under the vial accumulator 332, the accumulator 332 drops the vials into the assigned bin(s). The drop of the vials is effectuated by means of a release door contained in the accumulator position on which the vials rest and which is activated by a solenoid controlled by the control system. Preferably, the accumulator 332 is capable of placing its entire contents in one bin, if necessary. In this manner, all of the vials for one patient's order can be sorted and placed together in a bin.

When a patient's total order has been accumulated in one or more bin(s) 340, the sorting conveyor 242 transfers the bin(s) 340 to one of a plurality of spurs.

Spur 350 is a conveyor referred to as the exception conveyor. An order is placed on spur 350 if, for some reason, the contents must be modified due to error. Spur 350 can also be used to place medications other than oral solids into a patient's bin 340. This spur 350 can carry a bin 340 under a rack that contains, for example, liquids or creams. By reading the bar code on the bin 340, the rack automatically would discharge the correct medication into the bin 340.

Spur 352 is a conveyor referred to as the mail order conveyor. An order is placed on spur 352 if it is to be mailed to a patient. Spur 354 is a conveyor referred to as the pick-up conveyor. An order is placed on spur 354 if it is to be picked up by a patient, e.g. a walk-in.

As illustrated, a variety of extractors are operatively positioned to move bins onto and off of the conveyors 342, 350, 352, 360, and 361. These extractions are generally designated by the numeral 362. Extractor 362a, upon command, diverts bins from conveyor 342 into conveyor 350. Extractor 362b, upon command, diverts bins from conveyor 342 onto conveyor 352. Extractor 362c, upon command, diverts bins from conveyor 342 onto conveyor 354. Extractor 362d, upon command, diverts returned bins from conveyor 361 onto conveyor 360. Extractor 362e, upon command, diverts returned bins from conveyor 360 onto conveyor 342. Additionally, a scanner 363 is provided that reads bar codes on returned bins.

An empty bin 340 is placed on return conveyor 360 or 361 which places it back on circulating conveyor 342. Return conveyor 360 is used to return bins used for mail orders, while return conveyor 361 is used to return bins used for pick-up orders. At the point of return, the bar code on the bin (340) will be read and noted in the control system as an available bin. If the bar code is unreadable, the bin 340 is automatically ejected from the system 310. The return is located just downstream from the take-off on the circulating bin conveyor 342 so the circulating conveyor 342 will always be full. Overhead transfer cylinders 364 are used to transfer bins 340 from one straight conveyor 342a to another straight conveyor 342b, which together form the circulating conveyor 342.

In the above described conventional systems, in order to automatically and/or manually dispense medications and/or pharmaceuticals, the system must obtain large numbers of medications and/or pharmaceuticals from a variety of manufacturers using a variety of different stored bottles and/or packaging. The conventional systems shown in FIGS. 1-3 do not utilize, contemplate or suggest the use of a system that can automate the process of emptying the contents of manufacturers' drug carrying containers into a receptacle having a larger capacity, thereby simplifying the number and types of bottles that must be used for dispending pharmaceuticals.

SUMMARY OF THE INVENTION

Computer-assisted methods, systems and mediums of the present invention overcome, among others, the shortcomings of the above-described conventional systems.

In one embodiment, an automated system is provided for emptying contents of pharmaceutical containers, including medications. The system includes a gripper unit for receiving and holding a pharmaceutical container, a cutter for cutting the pharmaceutical container, and a rotating unit operable with the gripper unit that rotates at least a portion of the gripper unit to empty the contents of the pharmaceutical container, optionally into a bulk-up container. The pharmaceutical container can be of different shapes and sizes. The bulk-up container can comprise a substantially uniform sized container to facilitate the automated dispensing of the medications. The gripper unit can include first and second, optionally V-shaped, interlocking fingers.

The system can also include a robot for placing the pharmaceutical container in the gripper unit. A conveyor can also be provided that transports the pharmaceutical container in proximity to said robot.

In addition, a vision system can be utilized by the robot to facilitate determining the position of the pharmaceutical container on the conveyor. When the vision system does not recognize at least one of the size and shape of a pharmaceutical container, the pharmaceutical container is transported off the conveyor, optionally into a bin.

The cutter can be an ultrasonic cutter, with a blade that optionally moves in a direction substantially parallel to a belt of the conveyor. A rodless air cylinder is used to facilitate movement of the cutter.

The system can also include an arm that rotates to a first position to receive the cut portion of the pharmaceutical container. The arm can also rotate to a second position to facilitate placing the cut portion in a waste repository. The arm can include or utilize a vacuum that retains the cut portion of the pharmaceutical bottle when the arm is in the first position. The vacuum can decrease when the arm is in the second position to effect release of the cut portion into a scrap bin.

The system can also include a scrap chute that receives a portion of the pharmaceutical container subsequent to emptying the contents of the pharmaceutical container. The scrap chute can be in a distal position with respect to the gripper unit prior to emptying the contents of the pharmaceutical container. The gripper unit can move to a proximal position with respect to the gripper unit to receive the portion of the pharmaceutical container held by the gripper unit subsequent to emptying the contents of the pharmaceutical container. The scrap chute can return to the distal position to place the portion of the pharmaceutical container held by the gripper unit in a scrap bin.

The system can also include and/or utilize a sensor system to determine when the contents of the pharmaceutical container are no longer being emptied. In an embodiment, the sensor system can include a light emitter and a light receiver so that the light emitter provides a light beam that is broken by the contents of the pharmaceutical container when the contents of the pharmaceutical container are being emptied.

The system can also include a detection system to detect when the pharmaceutical container is no longer being held by the gripper unit. The detection system can include a light beam source and reflector, such that the reflector does not sense the light from the light beam source when the pharmaceutical container is held by the gripper unit.

A method for emptying the contents of pharmaceutical containers is also provided. In an embodiment, the method includes the steps of holding a pharmaceutical container for cutting, cutting the pharmaceutical container, and rotating the pharmaceutical container to empty the contents of the pharmaceutical container.

The method can also include the step of placing the pharmaceutical container in a waste repository subsequent to cutting. The method can also include the step of electronically viewing the pharmaceutical container prior to the holding and cutting steps. The viewing can provide position information of said pharmaceutical container.

The method can also include the step detecting when the contents of the pharmaceutical container are no longer being emptied. The method can also include the step of detecting when the pharmaceutical container is no longer being held.

In an embodiment, the system comprises means for receiving and holding a pharmaceutical container, means for cutting the pharmaceutical container, and means for rotating at least a portion of said the for receiving and holding to empty the contents of the pharmaceutical container. The system can also include means for placing the pharmaceutical container in the means for receiving and holding. In addition, the system can include means for transporting the pharmaceutical containers in proximity to the means for receiving and holding.

The system can also include means for viewing and determining the position of the pharmaceutical containers on the means for transporting. In addition, the system can include an arm that rotates to a first position to receive the cut portion of the pharmaceutical container, and a second position to place the cut portion in a waste repository.

The system can also include means for determining when the contents of the pharmaceutical container are no longer being emptied, as well as means for detecting when the pharmaceutical container is no longer being held by the means for receiving and holding.

In another embodiment of the present invention, an automated system for emptying the contents of pharmaceutical containers can include a gripper unit for receiving and holding a pharmaceutical container, a cutter for cutting the pharmaceutical container, and a control system for controlling the operation of the gripper unit and the cutter. The system can further include a rotating unit, operable with the gripper and the control system, that rotates at least a portion of the gripper unit to empty the contents of the pharmaceutical container.

The control system can include a keyboard, control logic, a display, and a processing unit. The control system can receive identification information of an operator of the system. The system can also include an indicia reader that interfaces with the control system. An indicia associated with a pharmaceutical container can be read by the indicia reader, and the control system can determine whether the pharmaceuticals are authorized.

The system can further include a robot that optionally interfaces with the control system, for placing the pharmaceutical container in the gripper unit. A vision system can be utilized by the robot, and optionally interface with the control system to determine, for example, the position of the pharmaceutical containers. The contents of the pharmaceutical containers can optionally be emptied into one or more bulk-up containers.

The system can also include an arm that optionally interfaces with the control system. The arm can rotate to a first position to receive a cut portion of the pharmaceutical container, and also rotate to a second position to place the cut portion in a waste repository. The arm can optionally utilize a vacuum that retains the cut portion of the pharmaceutical bottle when the arm is in the first position, and the vacuum can be reduced when the arm is in the second position to effect release of the cut portion.

The system can also include a scrap chute, optionally controlled by the control system, that receives a portion of the pharmaceutical container subsequent to emptying the contents of the pharmaceutical container. The system can also include a sensor system, optionally interfacing with the control system, to determine when the contents of the pharmaceutical container are no longer being emptied. The system can also include a detection system, optionally interfacing with the control system, to detect when the pharmaceutical container is no longer being held by the gripper unit.

In another embodiment of the present invention, a prescription filling and packing system can include a gripper unit for receiving and holding a pharmaceutical container, a cutter for cutting the pharmaceutical container, a rotating unit operable with the gripper unit that rotates at least a portion of the gripper unit to empty the contents of the pharmaceutical container into a storage container, and at least one dispensing machine that automatically counts and dispenses pharmaceuticals from the storage container and into bottles in accordance with prescription orders comprising at least one prescription.

The system can also include or utilize at least one printer for printing literature packs customized to the prescription orders. The system can also include or utilize at least one order consolidation and packing (OCP) station that presents a shipping container for each prescription order and inserts at least one bottle for each prescription order into the shipping container and inserts a corresponding literature pack for each prescription order into the shipping container.

The system can also include a gripper unit for receiving and holding a pharmaceutical container, a cutter for cutting the pharmaceutical container, a rotating unit operable with the gripper unit that rotates at least a portion of the gripper unit to empty the contents of the pharmaceutical container into a storage container, a plurality of carriers, each having receptacles to receive a plurality of bottles in scheduled locations, and at least one dispensing machine that counts and simultaneously dispenses pharmaceuticals from the pharmaceutical container and into at least one of the plurality of bottles.

The system can also include or utilize a computer that receives prescription orders for at least one prescription, as well as a loading station that loads the plurality of bottles in the scheduled locations corresponding to the prescription orders in at least one of said plurality of carriers.

The system can also include or utilize at least one transport device that transports the plurality of carriers with the plurality of bottles through at least one dispensing machine. The system can also include at least one order consolidation and packing (OCP) station that receives the plurality of carriers from the at least one dispensing machine and presents shipping containers to be filled. The at least one OCP station unloads the plurality of bottles from the plurality of carriers and loads at least one of the plurality of bottles and a corresponding customized literature pack corresponding to a prescription order into a shipping container. The literature pack and each of the bottles optionally have at least one corresponding identifier identified by at least one identification system to ensure that each of one or more bottles associated with the corresponding prescription order are inserted into the shipping container with the corresponding literature pack.

There has thus been outlined, rather broadly, the features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

Other features of the present invention will be evident to those of ordinary skill, particularly upon consideration of the following detailed description of the preferred embodiments.

Notations and Nomenclature

The detailed descriptions which follow may be presented in terms of program procedures executed on computing or processing systems such as, for example, a stand-alone computing machine, a computer or network of computers. These procedural descriptions and representations are the means used by those skilled in the art to most effectively convey the substance of their work to others skilled in the art.

A procedure is here, and generally, conceived to be a sequence of steps leading to a desired result. These steps are those that may require physical manipulations of physical quantities (e.g., combining various pharmaceutical products into packages). Usually, though not necessarily, these quantities take the form of electrical, optical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices, including, but not limited to, microprocessors.

BRIEF DESCRIPTION OF THE DRAWINGS

The detailed description of the present application showing various distinctive features may be best understood when the detailed description is read in reference to the appended drawings in which.

DETAILED DESCRIPTION OF THE INVENTION

Reference now will be made in detail to the presently preferred embodiments of the invention. Such embodiments are provided by way of explanation of the invention, which is not intended to be limited thereto. In fact, those of ordinary skill in the art may appreciate upon reading the present specification and viewing the present drawings that various modifications and variations can be made.

For example, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

Embodiments of the present invention are directed to dispensing orders that include various pharmaceutical products (e.g., bottles that contain counted pills, packages that include liquid or pre-packaged pharmaceutical products and/or patient specific literatures). In embodiments of the present invention pills also refer to tablets, capsules and other similar terms known in the art. As used herein, the term pill can also be used interchangeably with, for example, the terms tablet and/or capsule.

Figure 4A:
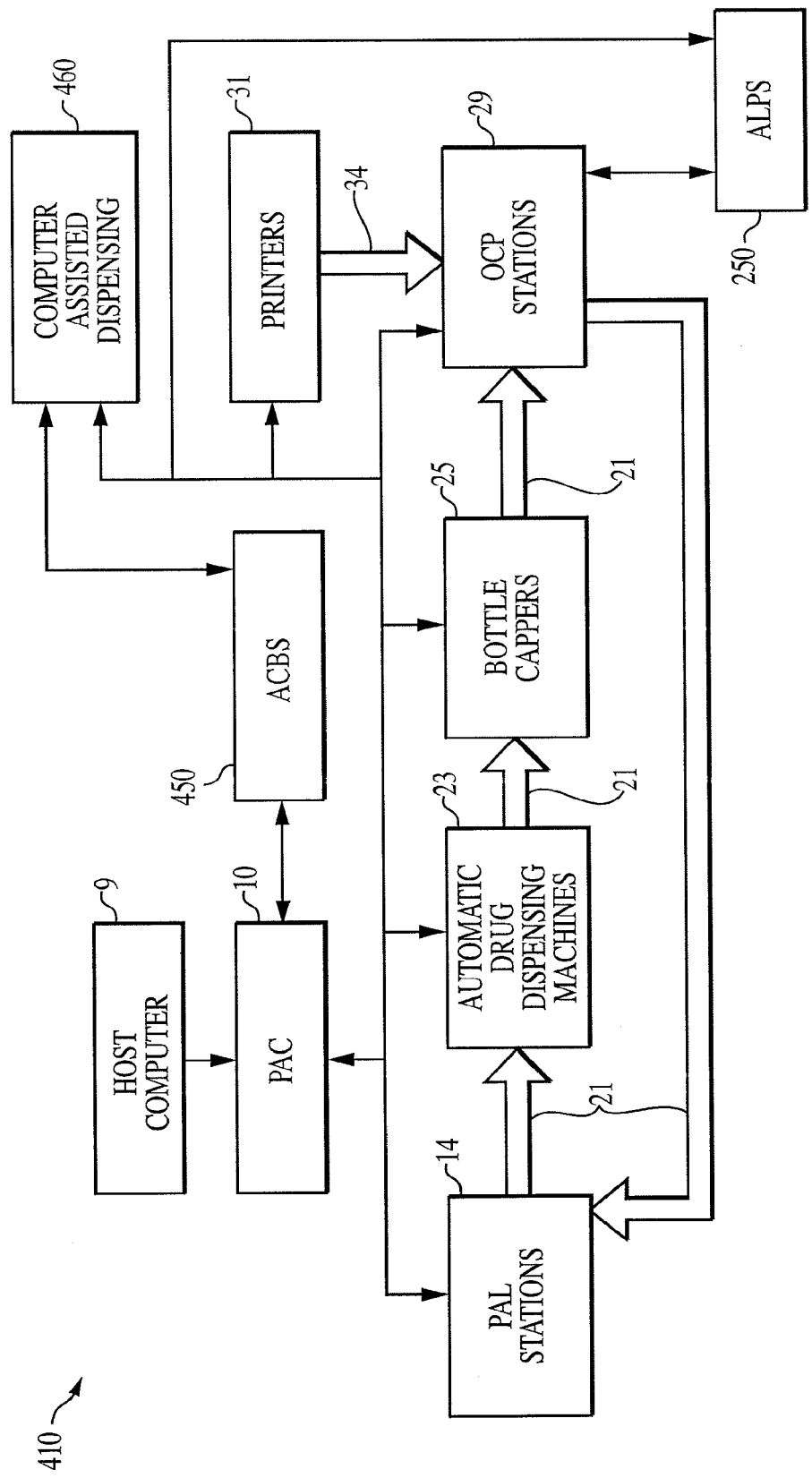
FIG. 4A is an exemplary diagram illustrating an embodiment of an automated pill dispenser in accordance with the present invention.

FIG. 4A is an exemplary diagram illustrating an embodiment of an automated pill dispensing system 410 in accordance with an embodiment of the present invention. In operation, orders (e.g., orders to fill prescriptions) are received by a host computer 9, which forwards the orders to a distributed computer system including a central computer called Pharmacy Automation Controller 10 (PAC). PAC 10 maintains an order file of the information about each prescription to be filled in an order including all of the information needed to fill each prescription, prepare a prescription label for each prescription and the information to print literature to go in a shipping container with the prescription or prescriptions. PAC 10 can update the order file to maintain a record of the current status of each prescription being filled as it progresses through the automated system.

PAC 10 controls a set of Print, Apply and Load (PAL) stations 14 which print prescription bottle labels, apply the prescriptions to prescription bottles, and load the labeled bottles onto bottle carriers. PAC 10 also controls a carrier conveyer system 21 which carries the bottle carriers to different parts of the system, automatic drug dispensing machines 23 which dispense tablets or capsules into the prescription bottles in the bottle carriers as they are carried by the conveyer system 21, bottle cappers 25 which apply caps to the bottles, and OCP stations 29 at which the bottles are unloaded from the carriers and placed in the shipping containers corresponding to the patient orders.

An Automated Container Bulking System (ACBS) 450 can also optionally interface with PAC 10. As will be described herein with regard to FIGS. 5-16, ACBS 450 can be used to empty the contents of, for example, manufacturers' drug bottles shown, e.g., in FIG. 9 at 910, into a bulk-up container shown, e.g., in FIGS. 13 and 14 at 1406, that have a larger capacity than individual bottles 910. Using bulk-up containers advantageously simplifies the number and types of bottles 910 that must be used with system 410. ALPS 250 can also optionally be integrated with system 410. In addition, a conventional Computer Assisted Dispensing System (CADS) 460 can optionally be integrated with, for example, ACBS 450, ALPS 250 and/or portions of system 410 such as, for example, PAC 10.

Conveyer system 21 carries patient prescription bottles in the carriers from the PAL stations through the automatic drug dispensing machines 23, to the bottle cappers 25, and then from the bottle cappers to the OCP stations 29. Conveyer system 21 also carries the empty carriers back to PAL stations 14. OCP stations 29 each also have a literature dispensing mechanism, which inserts printed literature into each shipping container with the filled and capped prescription bottles. PAC 10 controls literature printers 31 which print literature for each prescription order and enclose the literature for each prescription order in an envelope, print a bar code that shows through a window in the envelope identifying the prescription order. PAC 10 can also control placement of each envelope on a literature conveyer (not shown), which carries the envelope from the literature printers 31 to the OCP stations 29.

Figure 1A:
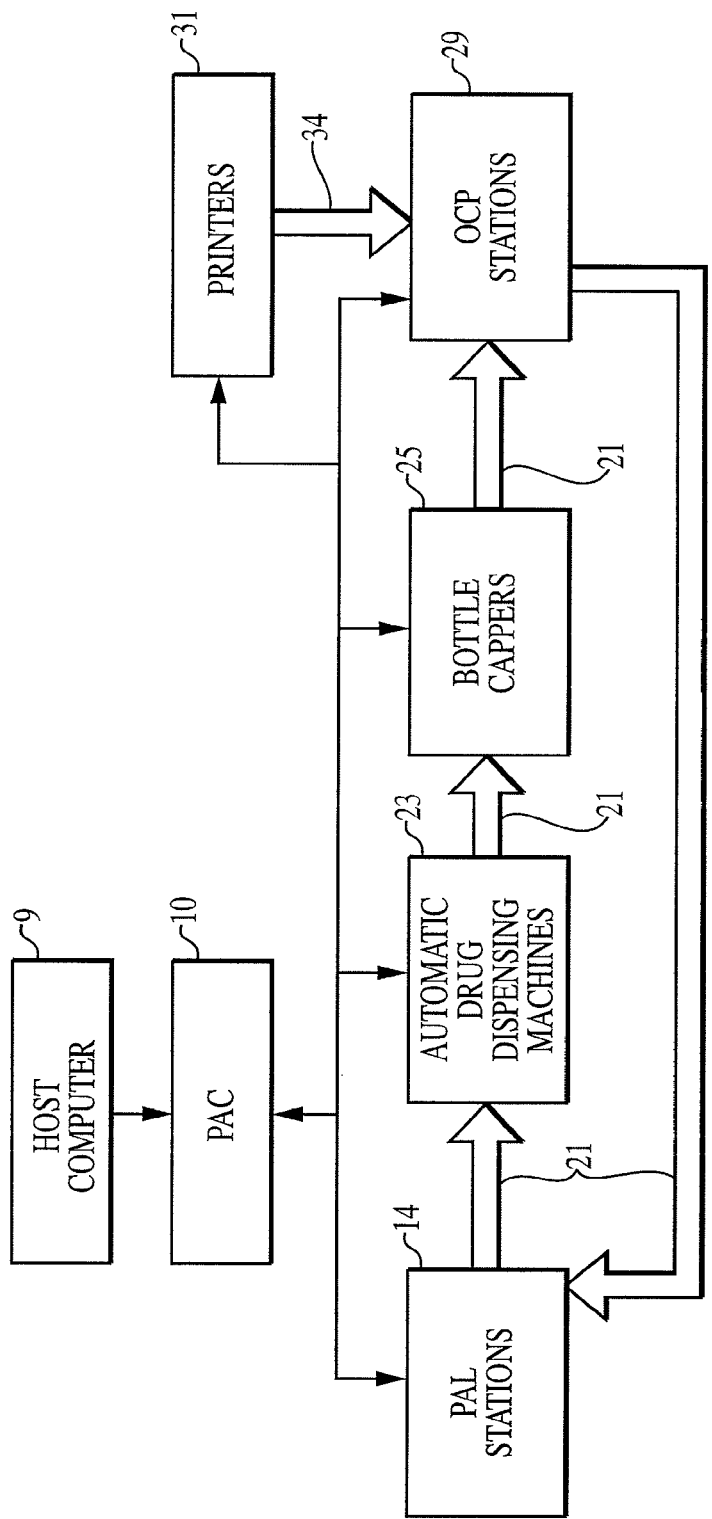
FIGS. 1A and 1B are exemplary diagrams illustrating a conventional automated pill dispenser.
Figure 1B:
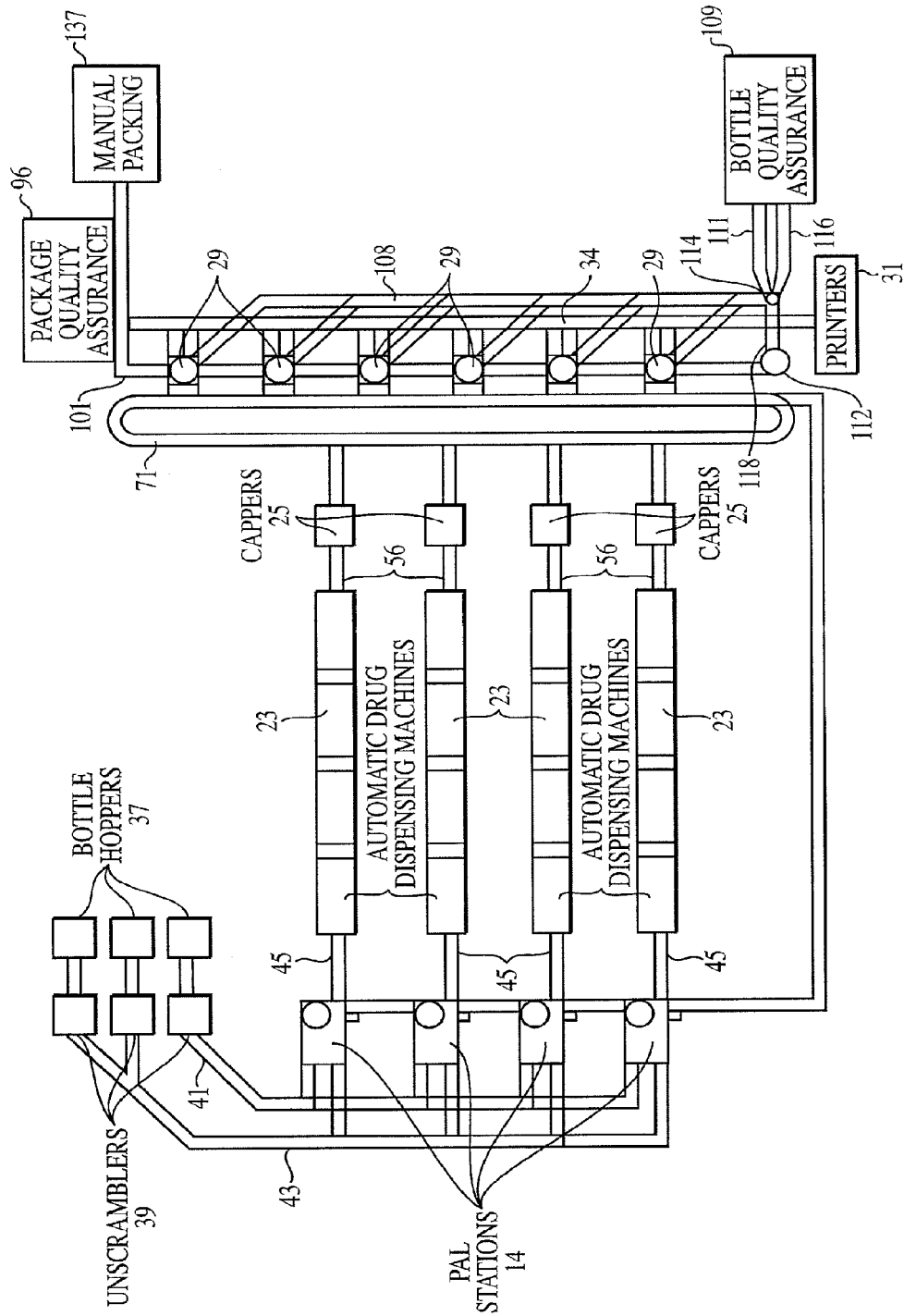
Figure 2:
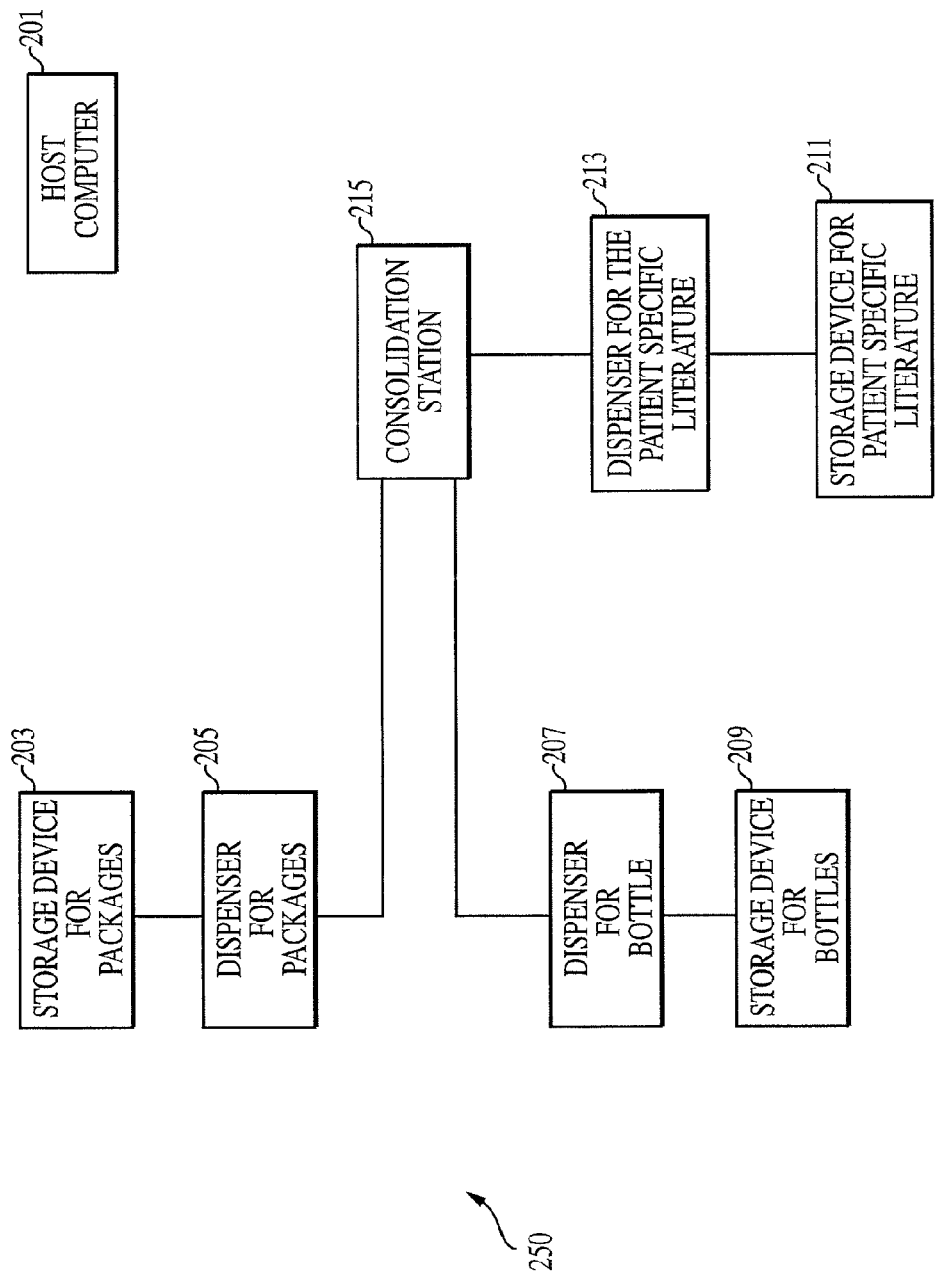
FIG. 2 is an exemplary diagram illustrating a second conventional automated pill dispenser.
Figure 3:
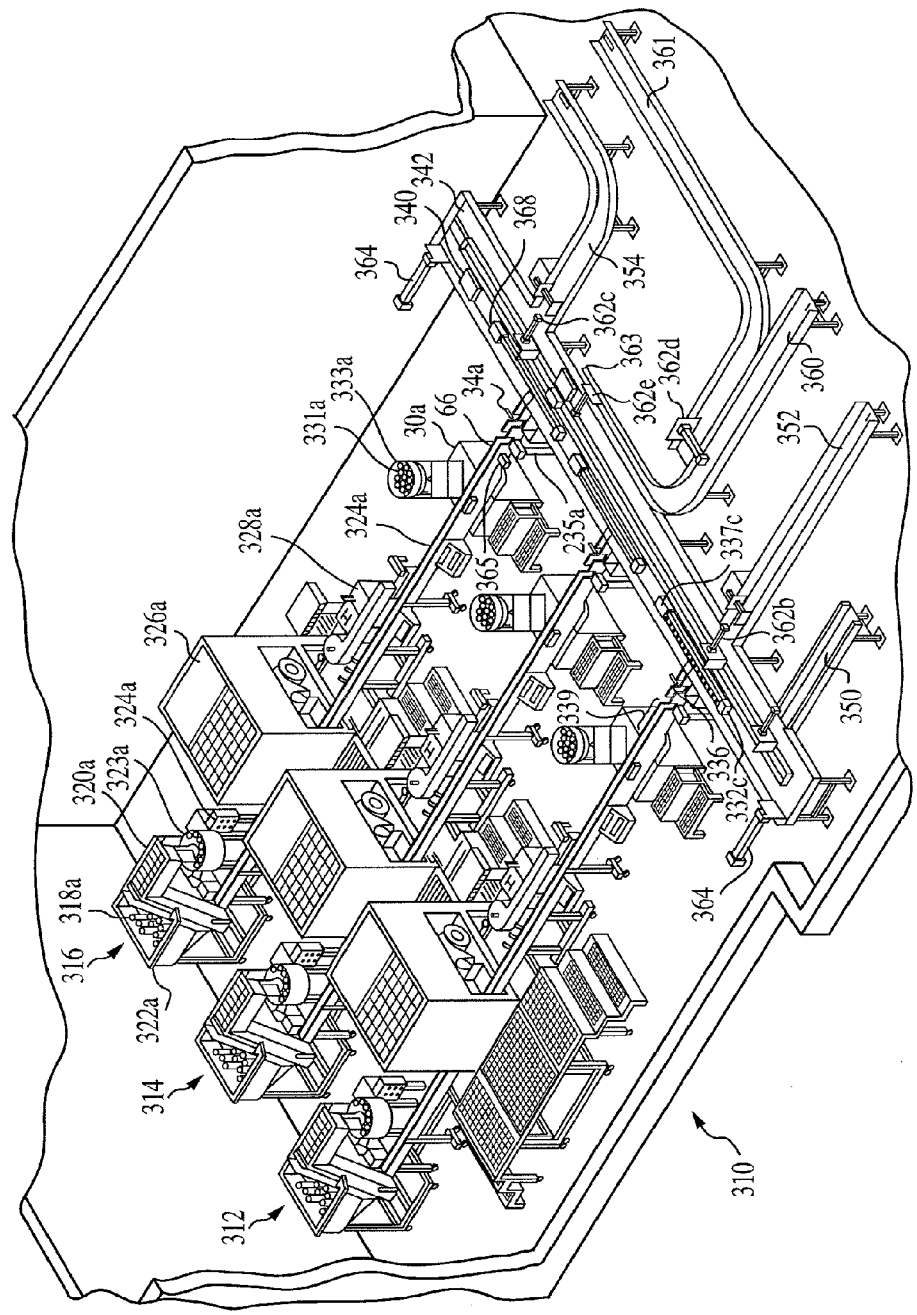
FIG. 3 is an exemplary diagram illustrating a third conventional automated pill dispenser.

Patient prescription bottles that are to be automatically filled with the prescription drugs can be introduced to the automated system by hoppers (not shown, but the same as or similar to hoppers 37 shown in FIG. 1B) which receive the bottles in bulk form and automatically feed the bottles to unscramblers 39. One hopper 37 and one of the unscramblers (not shown, but the same as or similar to an unscrambler 39 shown in FIG. 1B) can be used for relatively large bottles (e.g. 160 cc), and the remaining hoppers and unscramblers can be used for small bottles (e.g., 110 cc). Small bottles preferably an be used for a majority of the prescriptions. Any prescription orders that cannot be filled by using a large bottle can be filled by using multiple large and/or small bottles. In the unscramblers, the bottles are singulated and oriented so that the bottle opening first faces downward. The bottles are then righted and directed to PAL stations 14 on bottle conveyers (not shown, but the same as or similar to conveyors 41, 43 shown in FIG. 1B), one for large bottles and one for small bottles.

Figure 4B:
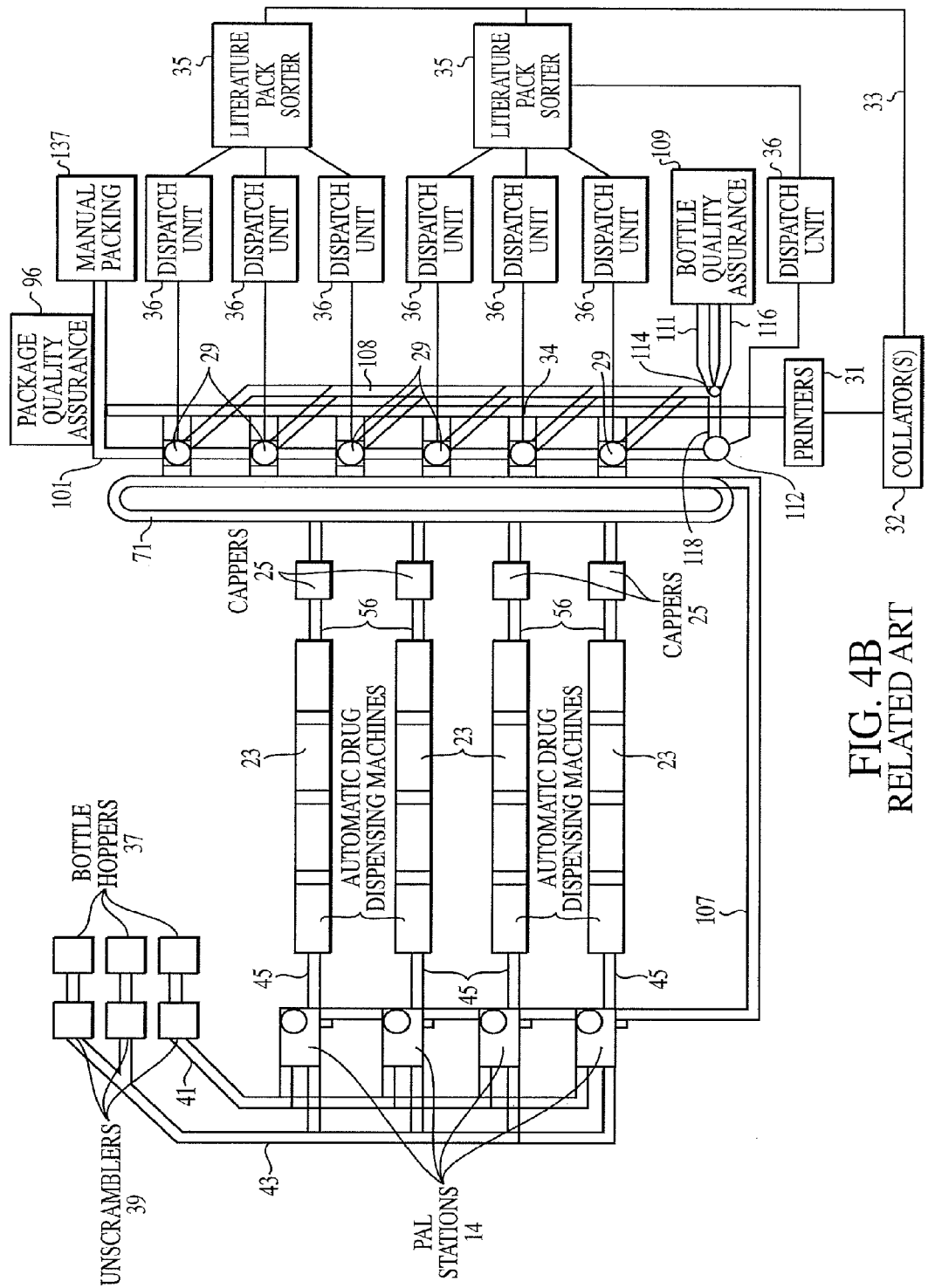
FIG. 4B is an exemplary diagram illustrating an aspect of an automated pill dispenser that can be used with the present invention.

FIG. 4B is similar to FIG. 1B, and shows exemplary aspects of the automated pill dispensing system 410 shown in FIG. 4A. In operation, one or more literature packs can be printed on a printer 31, and sent to a collator 32 for collation into individual literature packs. More than one collator 32 can optionally be used. Once literature packs are collated, they can travel, for example, on a standard pinchbelt conveyor 33 to a literature pack sorter 35, where they are sorted into literature pack batches. Although two literature pack sorters 35 are shown, any number of literature pack sorters can be utilized to suit, for example, cost and/or volume considerations.

On command from, for example, an OCP station 29, the literature pack batches can optionally be manually transferred from the one or more sorters 35 to a dispatch unit 36. Again, any number of dispatch units can be utilized to accommodate, for example, manufacturing, facility size and/or cost requirements or constraints. Dispatch units 36 can feed the literature packs to an OCP station 29.

When system 410 detects (and/or suspects) a problem with an order (e.g., a wrong shipping address, incorrect prescription drug(s), and/or incorrect prescription quantity), an OCP station 29 can place the order in a bag, and divert the bag into, for example, a standard tote (not shown). The tote can be transported by, for example, conveyer 101 to package quality assurance station 96, where a quality assurance person can inspect the order and correct anything that might be wrong (as discussed above) with the order. After inspection and corrective action, the quality assurance person at station 96 can take additional action(s) to ensure that the properly filled order is shipped to the patient/client.

Figure 5:
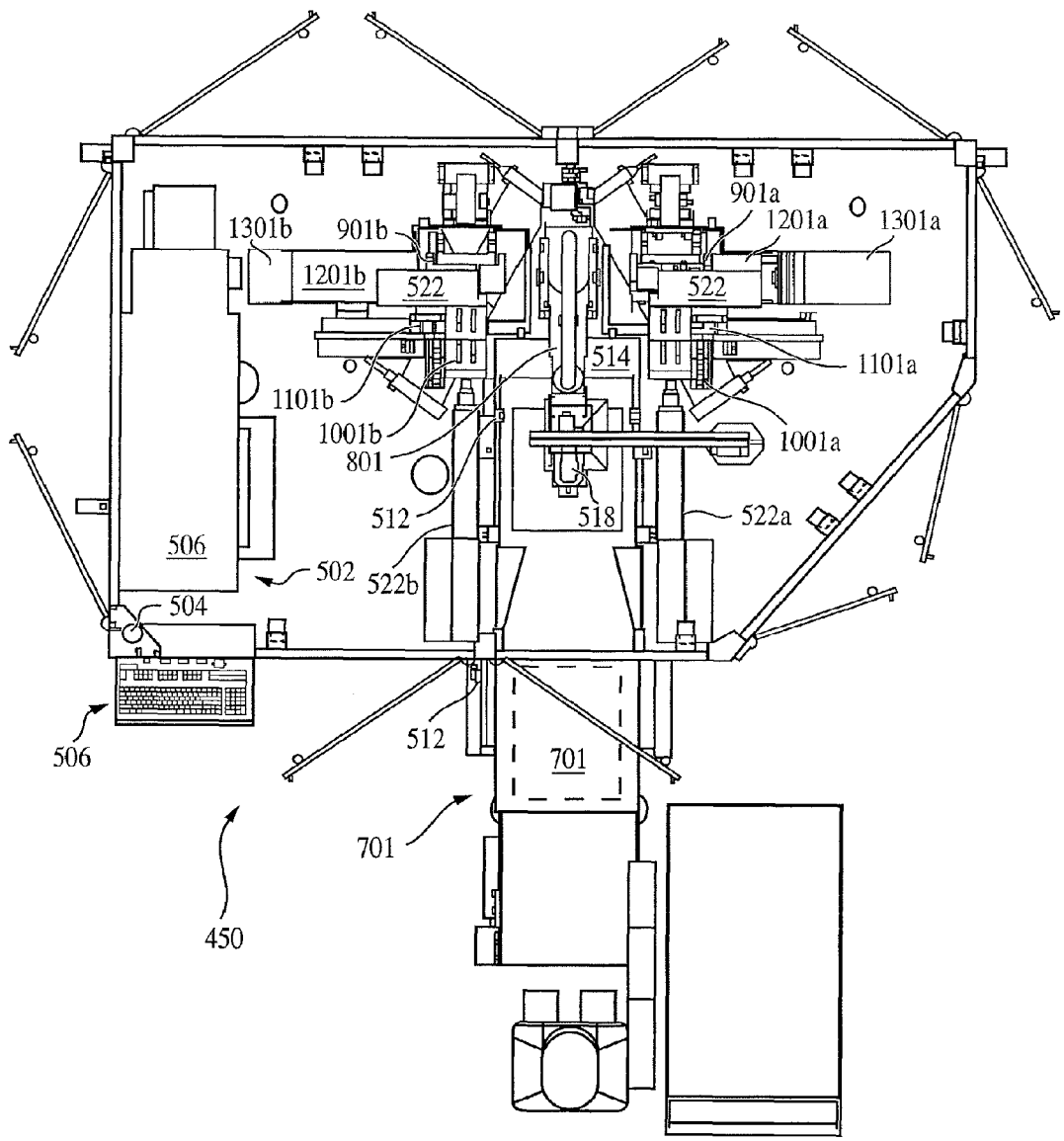
FIG. 5 is an exemplary top view of an embodiment of the Automated Container Bulking System (ACBS)
Figure 6A:
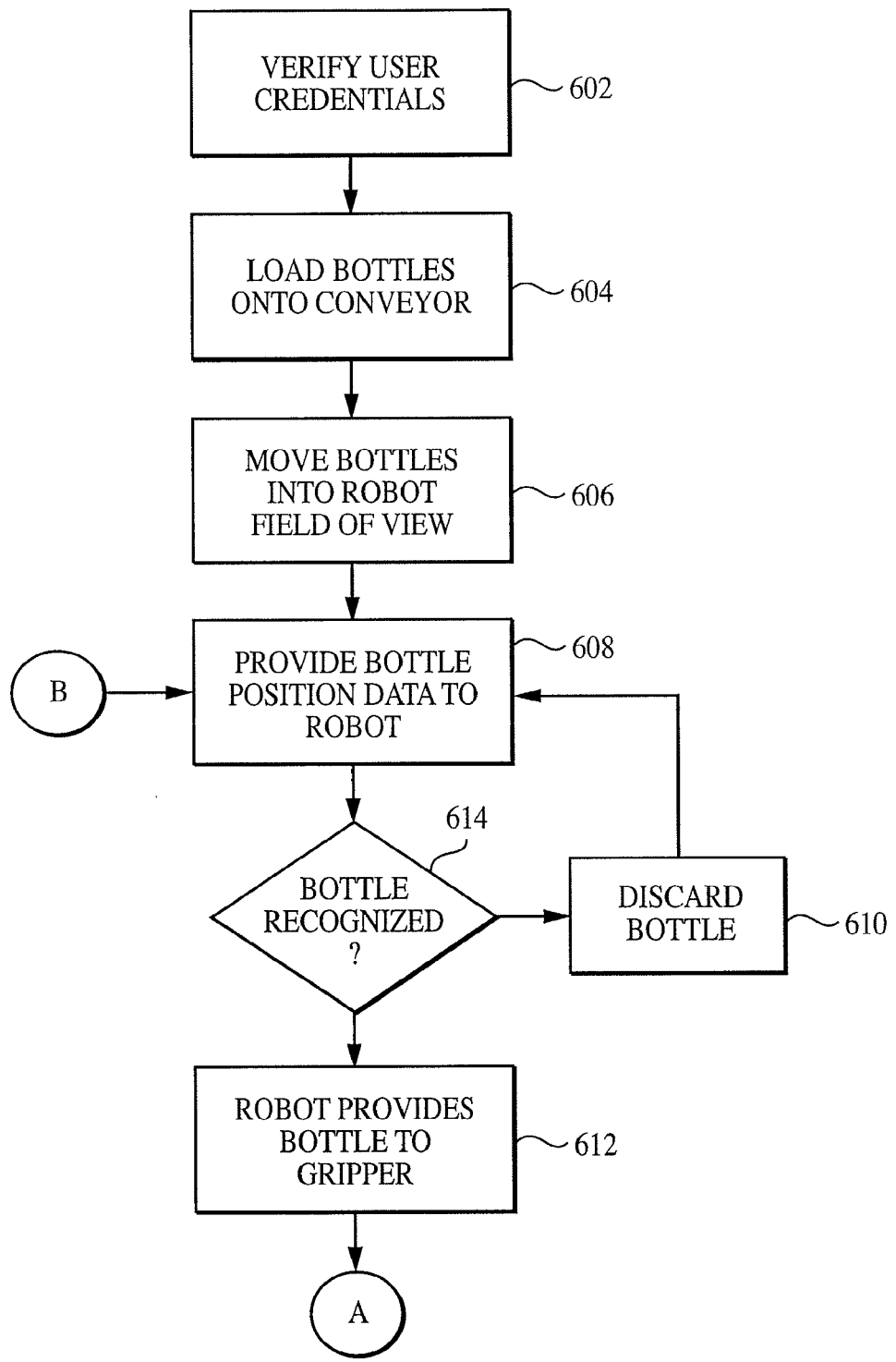
FIGS. 6a and 6b, taken together, is an exemplary embodiment of a flow diagram in accordance with a method of operation of the ACBS.
Figure 6B:
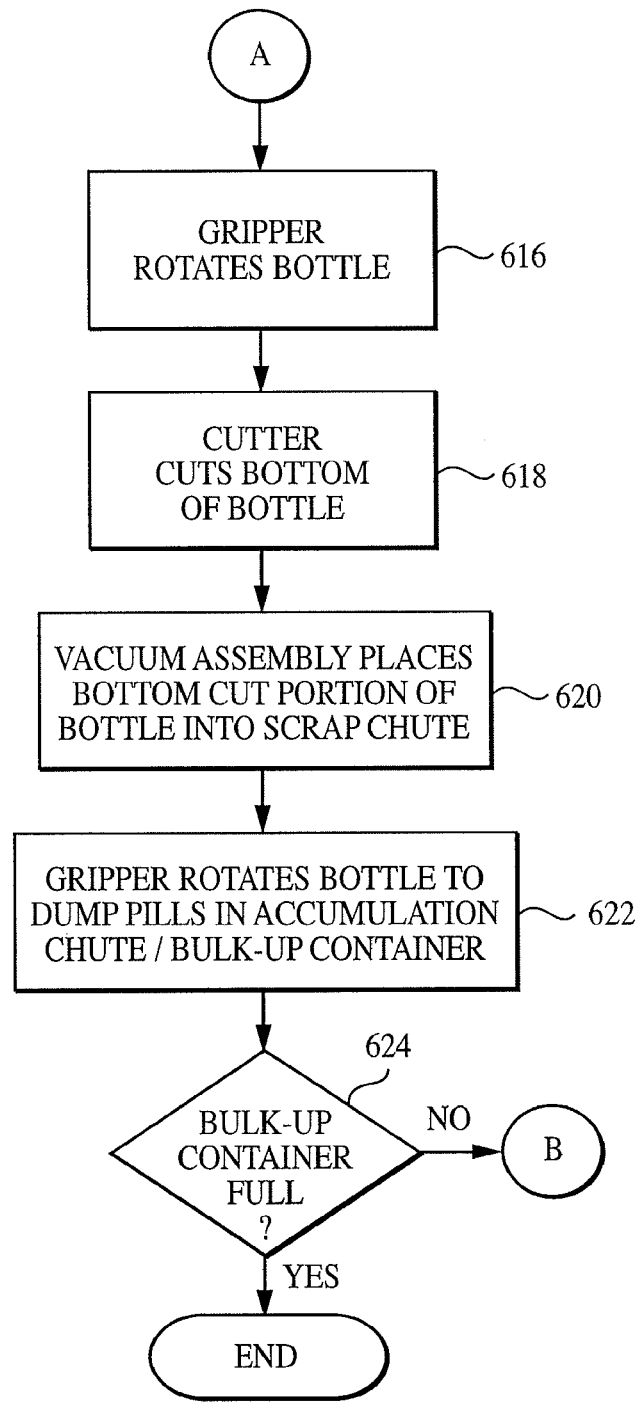

Operation of ACBS 450 may be best understood with simultaneous reference to FIG. 5, which depicts a top view of an embodiment of ACBS 450, and FIG. 6, which depicts an embodiment of a flow diagram in accordance with a method of operation of ACBS 450. Reference hereafter will also be made to FIGS. 7-16, each of which are related to FIGS. 5 and 6.

System 501 automates the process of emptying the contents of manufacturers' bottles 910 into a bulk-up container 516 having a larger capacity than individual bottles 910. Bulk-up containers 516, in turn, can be utilized in conjunction with, for example, dispenser for bottles 207.

In general, system 501 optionally comprises two (or more) "sides" (e.g., side 1 and side 2). In FIG. 5, certain components are indicated as having "a" and "b" elements (e.g., 901a and 901b; 1001a and 1001b, etc.). The "a" and "b" elements respectively correspond to sides 1 and 2 of system 501. Sides 1 and 2 expedite processing, as well as provide for redundancy in the event that one side is not available (e.g., for maintenance). The present invention also envisions three or more "sides" that can be utilized and provided in an integrated system 501. An embodiment of system 501 comprising a single side can also be utilized.

System 501 is optionally initialized by verifying user credentials at step 602. For example, control system 506 can comprise an instruction banner that optionally displays, for example, Scan and/or Enter Employee ID for Current Bulk-up Container. Control system 506 can optionally include, for example, a keyboard, personal computer (PC), display monitor and/or reader with which an operator can, for example, scan his/her badge and/or enter his/her password.

In addition, control system 506 can also optionally display, for example, Scan or Enter National Drug Code (NDC) for a bulk-up container 1406 (shown in FIG. 14) that is to be utilized with side 1 or side 2. In an embodiment, an operator can scan the drug NDC from a bottle 910 by using barcode scanner 512.

Control system 506 can also optionally display, for example, Enter Expiry Date for NDC. An operator can then enter a valid expiry date, which can be utilized to ensure that (legally) authorized drugs are being utilized. If the expiry date falls within a predetermined date of the current date (e.g., within six months of the current date), an override password (or other override mechanism) can optionally be utilized.

Control system 408 can also optionally display, for example, Enter Lot Number for NDC, whereupon an operator can enter a valid lot number. Upon verifying user credentials and optionally performing other set-up operations (as described above), an operator can place a bulk-up container 1406a (and/or 1406b) in a position so that it respectively receives pills from pill chute 1301. Each side of system 501 preferably has its own pill chute 1401a, 1401b. Thus, in the embodiment shown in FIG. 5, a first pill chute (1401a) is utilized for side 1, and a second pill chute (1401b) is utilized for side 2.

A multi-colored beacon 504 can optionally be provided, preferably but optionally in the vicinity of control system 506, to indicate various states of system 450. For example, a green beacon can be solid when system 450 is in automatic mode, and flash when system 450 is in manual mode (where, e.g., an operator may manually want to control robot 801). An amber beacon can flash when system 450 is low on supplies (e.g., bottles 910). A red beacon can be solid to indicate that an emergency stop button has been pressed, and/or that a guard door has been opened. A red beacon can flash to indicate that a fault exists (e.g., conveyor belt 704 is not in operation). Any color scheme can be used. In addition, beacon 504 can also include additional color(s) to indicate (or correspond) other states or operating status of system 450 or subsystems thereof.

The control system 506 PC can utilize software (e.g., Microsoft Access®) to provide and/or access various databases (e.g., one or more drug databases, one or more employee databases, one or more end report databases, and the like). In an embodiment, control system 506 PC can also optionally utilize, for example, a RS-232 connection to interface with scanner 512. The PC can read scanner signals, and verify that the drug is a valid drug as indicated by, for example, one or more the drug databases.

In addition, control system 506 PC can optionally utilize, for example, a conventional Ethernet connection to interface with robot 801, vision system 518 and/or one or more vacuum valves and/or sensors associated with, for example, robot 801. Further, control system 506 PC can also optionally utilize the same or a different Ethernet connection to interface with cutter assembly 1002, conveyor 701 control system and/or various vacuum systems that can optionally be utilized to minimize, for example, pill dust that may be generated when bottles 910 are emptied and/or when bulk-up containers 1406 are removed.

Control system 506 can also optionally comprise, utilize and/or generate various screen displays and/or touch screen menus that allow an operator to, for example, enter various data and/or control the operation of system 450. For example, system 450 can utilize and/or generate, for example, run status screen(s) and/or menu(s), manual control screen(s) and/or menu(s), scanner 512 setup screen(s) and/or menu(s), beacon 604 status and/or control screen(s) and/or menu(s), alarm history and/or status screen(s) and/or menu(s), robot control and/or status screen(s) and/or menu(s), drug data entry screen(s) and/or menu(s), employee data entry screen(s) and/or menu(s), end report screen(s) and/or menu(s), change operator screen(s) and/or menu(s), employee password screen(s) and/or menu(s), drug expiry date screen(s) and/or menu(s) and/or other various system status and/or control screen(s) and/or menu(s).

Figure 7:
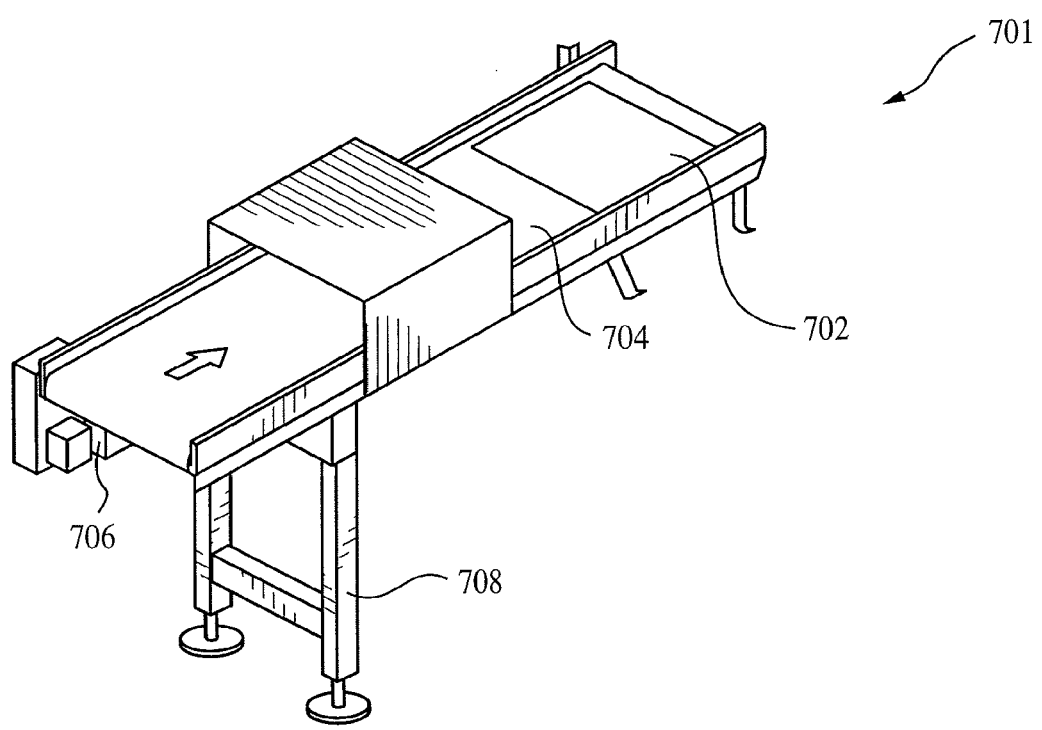
FIG. 7 is an exemplary embodiment of an infeed conveyor of the ACBS.

At step 604, bottles 910 are loaded onto conveyor 701, preferably with the lids (e.g., a twist cap, not shown) facing up. An exemplary embodiment of conveyor 701 is shown in FIG. 7. In an embodiment of system 450, a Dorner 800 series flatbelt infeed conveyor (from Dorner Mfg. Corp., Hartland, Wis.) can be utilized, which includes an illuminated end 702, a belt 704, a gear motor 706, and a support stand 708. Conveyor 701 also preferably comprises a control system (not shown) that can optionally interface and/or be integrated with control system 506.

Scanner 512 (e.g., a barcode scanner) allows an operator to, for example, scan a bottle 910 (optionally representative of a batch of bottles). Scanner 512 can also be used to scan, for example, an operator ID. Scanner 512 can be manufactured by, for example, Datalogic S.p.A., Bologna, Italy. The bottle barcode (or other identifier) preferably and typically indicates the drug and bottle type, which allows control system 508 to access any relevant bottle 910 data from, for example, a database (as previously discussed).

At step 606, conveyor belt 704 can be used to move one or more bottles 910 into view of vision system 518, which is utilized in conjunction with robot 801. In particular, vision system 518 can be mounted overhead of robot 801 to view bottles 910. Vision system 518 is preferably positioned over illuminated conveyor end 702, which facilitates viewing. Illuminated conveyor end 702 is preferably illuminated from below belt 704 to assist robot 801 in picking a bottle 910 from conveyor 701. At step 608, vision system 518 can relate, for example, position and/or orientation information of one or more bottles 910 to robot 801.

At decision step 612, a determination can be made regarding whether system 450 recognizes each bottle 910. Multiple bottle 910 sizes and shapes can be utilized. For example, vision system 518 can optionally verify that bottles 910 are of the correct diameter and/or overhead shape. If a bottle 910 size and/or shape is not recognized, robot 801 will not pick-up the bottle 910, and the bottle 910 can be discarded at step 610, after which updated bottle 910 position data is provided to robot 801 at step 608. In an embodiment of system 501, bottles 910 that are not recognized (e.g., wrong bottle, wrong size/shape, bottle fallen over) by vision system 518 are driven off the end of the conveyor 701 into bottle return bin 410. An operator can empty bottle return bin 910 and reload the proper bottles (e.g., fallen over bottles) 910 onto conveyor 701.

If, at decision step 612, a bottle 910 is recognized, robot 801 provides the bottle 910 to a gripper assembly 901a, 901b. As previously noted, an embodiment of system 450 comprises two "sides" (e.g., side 1 and side 2). If both sides are in operation, system 450 can operate, for example, in a round-robin mode, where robot 801 will alternate each bottle 910 between gripper 901a and 901b. In the alternative, a single side (e.g., gripper 901a or gripper 901b) can be used until the bulk-up container associated with that side is full, and then switch to the other side (which presumably has a bulk-up container that is not full). If, for any reason, only one side of system 450 is being utilized, robot 801 will place bottle 910 in the gripper 901 of the side that is being utilized.

In an embodiment, robot 801 can have or utilize a vacuum in the vicinity of gripper assembly 901 to draw, for example, an end of bottles 910 in closest proximity to robot 801 to facilitate picking bottles 910 off of conveyor 701.

At step 614, robot 801 places bottle 910 onto a reciprocating bottle platform 1204 upon which a surface of bottle 910 rests. Bottle platform 1204 is positioned beneath grippers 908a, 908b so that bottle 910 rests on the platform 1204 prior to grippers 908a, 908b gripping the bottle. In a second position, and coincident with or subsequent to gripping, bottle platform 1204 is moved away from grippers 908a, 908b so that the contents of bottle 910 can subsequently be emptied into bulk-up container 1406 positioned therebelow.

At step 616, rotate mechanism 914 is used to rotate bottle 910 into an upside down orientation (e.g., with the capped end facing down). Vacuum assembly 1101 is positioned near gripper assembly 901 so that suction plate 1110 can be positioned over the base of the bottle (e.g., the cutting area) when bottle 910 is in the upside down orientation.

At step 618, one of cutter assembly 1001a, 1001b is used to cut bottle 910. In an embodiment, cutter assembly 1001a, 1001b can comprise an ultrasonic system (Branson Ultrasonics Corporation, Danbury, Conn.) with a vibrating cutter 1002 that cuts through a bottle. Cutter 1002a, 1002b can be advanced by pneumatic actuator 522a, 522b so that blade 1006 cuts bottle 910. In particular, suction plate 1110 holds the bottom of a bottle as cutter 1002a, 1002b advances. As blade 1006 cuts at or near an end of a bottle, the cutting action raises the cut portion of the bottle to suction plate 1110, which draws the cut portion of the bottle 1112.

After the bottle is cut, rotary actuator 1106 is then actuated to rotate rotary arm 1108 so the bottle scrap 1112 can be placed on one of scrap chute 1201a, 1201b (shown in FIG. 5), which feeds the bottle scrap 1112 to one of bottle scrap bin 1301a, 1301b. Grippers 908a, 908b then rotate bottle 910 approximately 180° so that the contents of bottle 910 are emptied onto an accumulation chute 1401 (as shown, e.g., in FIG. 14), which leads to a bulk-up container 1406. Vacuum hoods 522a, 522b are optionally provided, preferably near cutters 1002a, 1002b, to minimize pill dust cross product contamination and/or to control pill dust from spreading. Vacuum capture velocities can be set at, for example, approximately 100 feet per minute.

Once the contents of the bottle 910 have been emptied, one of scrap chute 1201a, 1201b advances to receive the remaining portion of bottle 910, which is dropped thereon by one of gripper assembly 901a, 901b. One of scrap chute 1201a, 1201b retracts and the remaining portion of bottle 910 is placed into one of scrap bin 1301a, 1301b.

When a bulk-up container 1406 is full, an End Report can optionally be created. An end report can indicate, for example, the drug NDC number, the drug expiry date, the number of pills emptied into a bulk-up container 1406 and/or the time the bulk-up container 1406 stopped receiving additional contents from bottles 910. An operator can remove bulk-up container 1406, and can choose to run the same drug again or scan a different drug.

In an embodiment, when multiple bulk-up containers 1406 are utilized, the following procedure can be used. When system 450 is processing a bulk-up container 406, a NEXT BULK-UP IS SAME NDC pushbutton (or other actuator) on a Run Status screen can be presented to an operator at, for example, control system 506. When the pushbutton is pressed, a pop up box, for example, can be displayed that instructs the operator to scan the next bulk-up container 1406.

When the current bulk-up container 1406 is finished, a message can be displayed that instructs an operator to change bulk-up container 1406. The operator then replaces the existing (full) bulk-up container 1406 with the new one.

Preferably near each pill accumulation chute 1401a, 1401b a LOAD EMPTY BULK CONTAINER pushbutton (or other actuator) is provided. The pushbutton can, for example, flash slowly when the current bulk-up container 1406 is full.

Once an operator has placed a new pre scanned-in bulk-up container 1406 underneath a pill accumulation chute 1401a, 1401b, the corresponding pushbutton can flash rapidly, indicating that the pushbutton should be pressed to acknowledge that a new bulk-up container 1406 has been placed under a pill accumulation chute 1406a, 1406b.

Once an operator has scanned the new bulk-up container 1406 (using, e.g., barcode scanner 512) and has placed it underneath pill accumulation chute 1401, another pushbutton, for example, can be pushed to continue processing. For example, a LOAD EMPTY BULK CONTAINER pushbutton (of control system 506) can be pushed to continue processing the existing NDC drug. Of course, actuators other than pushbuttons can also be utilized.

Figure 8:
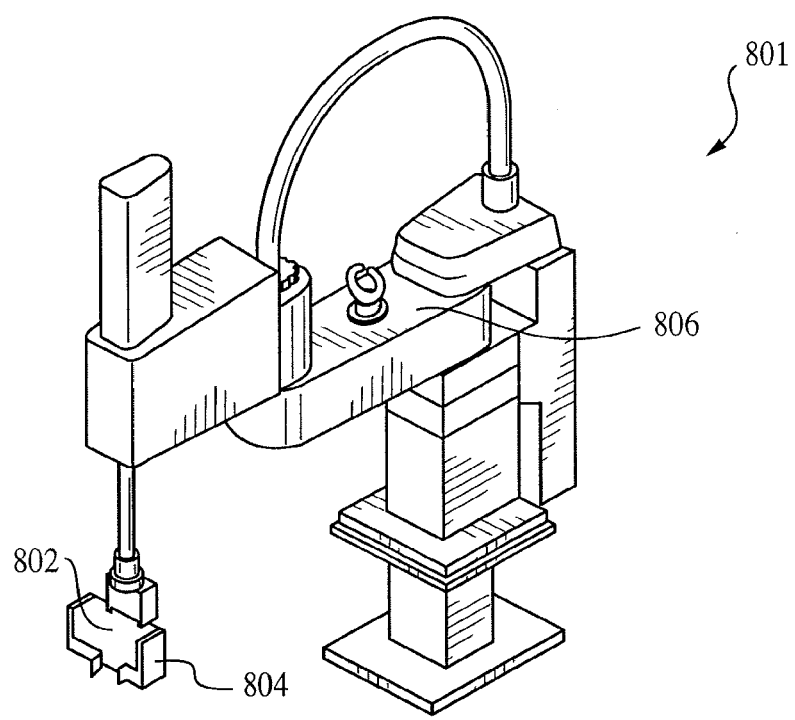
FIG. 8 is an exemplary embodiment of a robot of the ACBS.

FIG. 8 is an exemplary embodiment of a robot 801 of the ACES 501. In an embodiment, robot 801 can be an Adept Cobra 600 robot (Adept Technology, Livermore, Calif.) that accommodates x, y, z, and theta movements. The height of the bottles is optionally downloaded to control system 506 based on the NDC of bottles 910, which can be scanned by barcode scanner 512. Robot 801 preferably but optionally has a vacuum end of arm tool (EOAT) that draws the end of the bottle 910 in closest proximity to the robot, and picks the bottle 910 off of the conveyor 701. The EOAT can handle bottles 910 of varying size and/or diameter. Once a bottle 910 has been selected, robot 801 grasps, for example, the cap of a bottle 910, optionally rotates the bottle 910 to the correct orientation, and places it into one of the two gripper assemblies 901a, 901b.

Vision system 518, which is preferably placed over illuminated conveyor end 902, can be used to facilitate viewing bottles 910 and relaying, for example, location and orientation information of bottles 910 to robot 801. Vision system 518 also verifies that the bottles 910 are, for example, the correct diameter and/or overhead shape. Vision system 518 can include a camera available from, for example, PULNiX America, Sunnyvale, Calif.

FIGS. 9a-9d show various views of an exemplary embodiment of gripper assembly 901a, 901b, which comprises interlocking fingers 908a, 908b that are capable of movement to grip and release bottle 910. In an embodiment, fingers 908a, 908b are V-shaped. Rotate mechanism 914 can include belt 916, drive pulley 918, and timing belt 920, which allows gripper assembly 901a, 901b to rotate (e.g., 180°) to empty bottle 910 contents into a pill accumulation chute 1401a, 1401b.

Figure 9A:
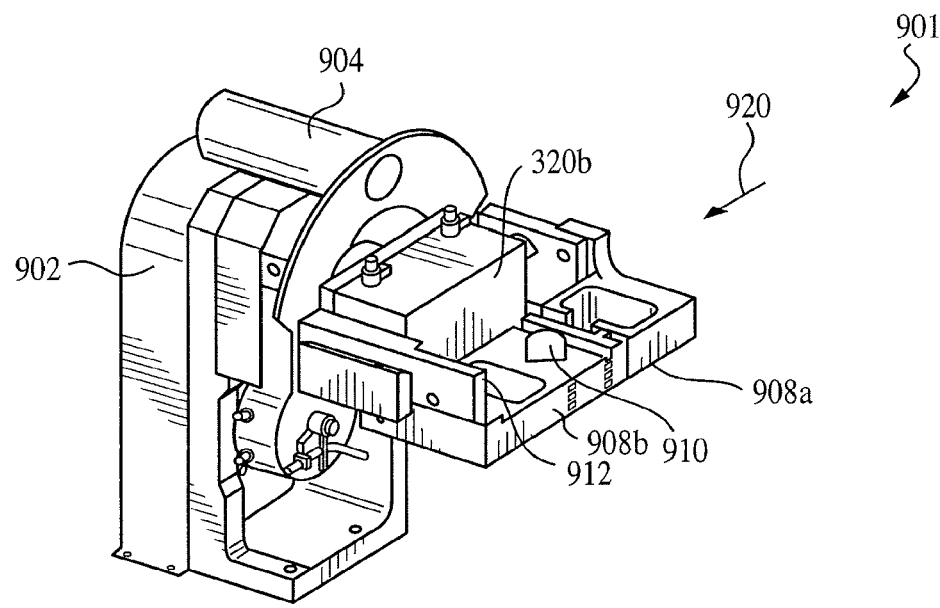
FIGS. 9a-9j are various views of an exemplary embodiment of the grippers of the ACBS, and bottle positions within the grippers.
Figure 9B:
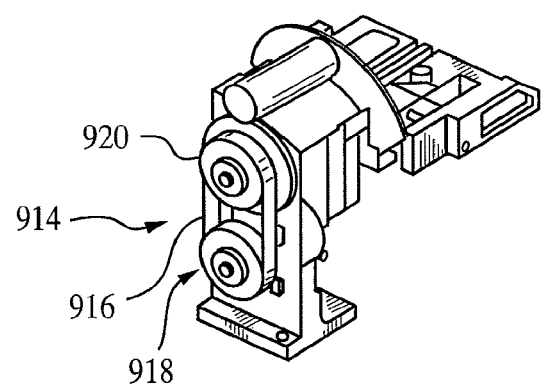
Figure 9C:
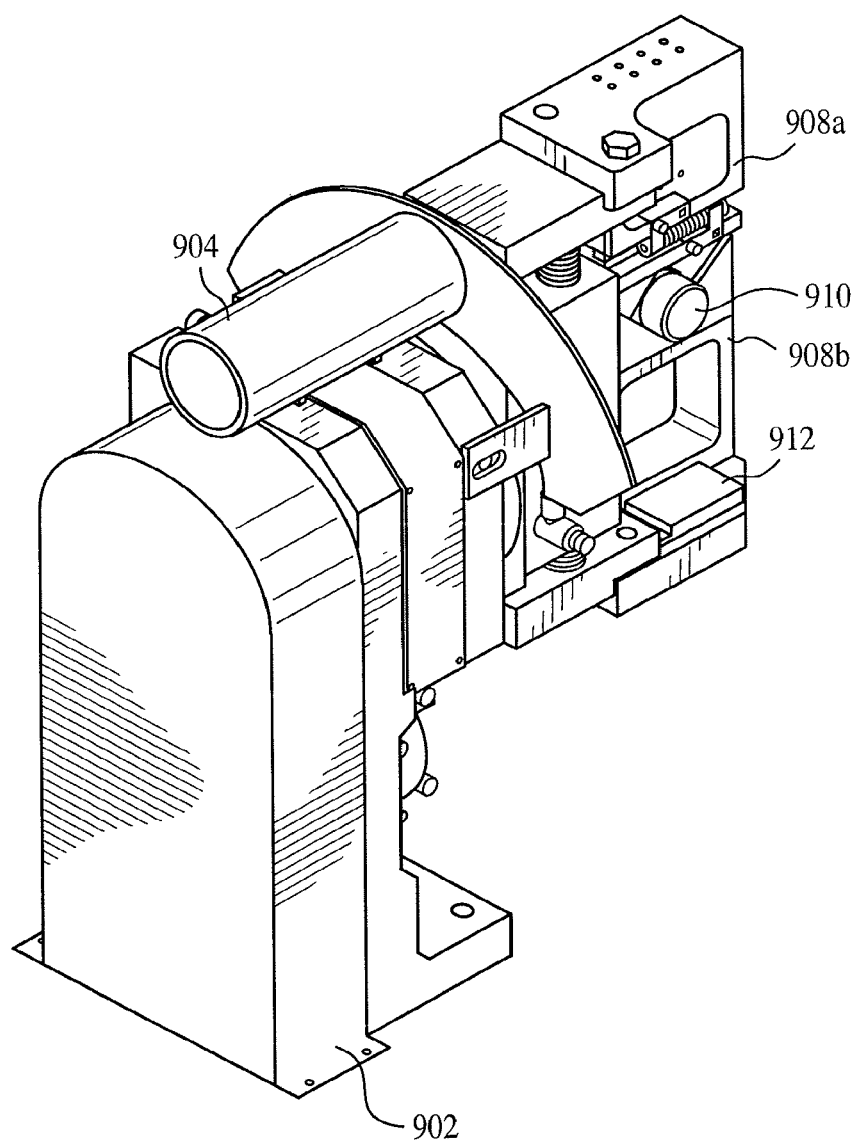
Figure 9D:
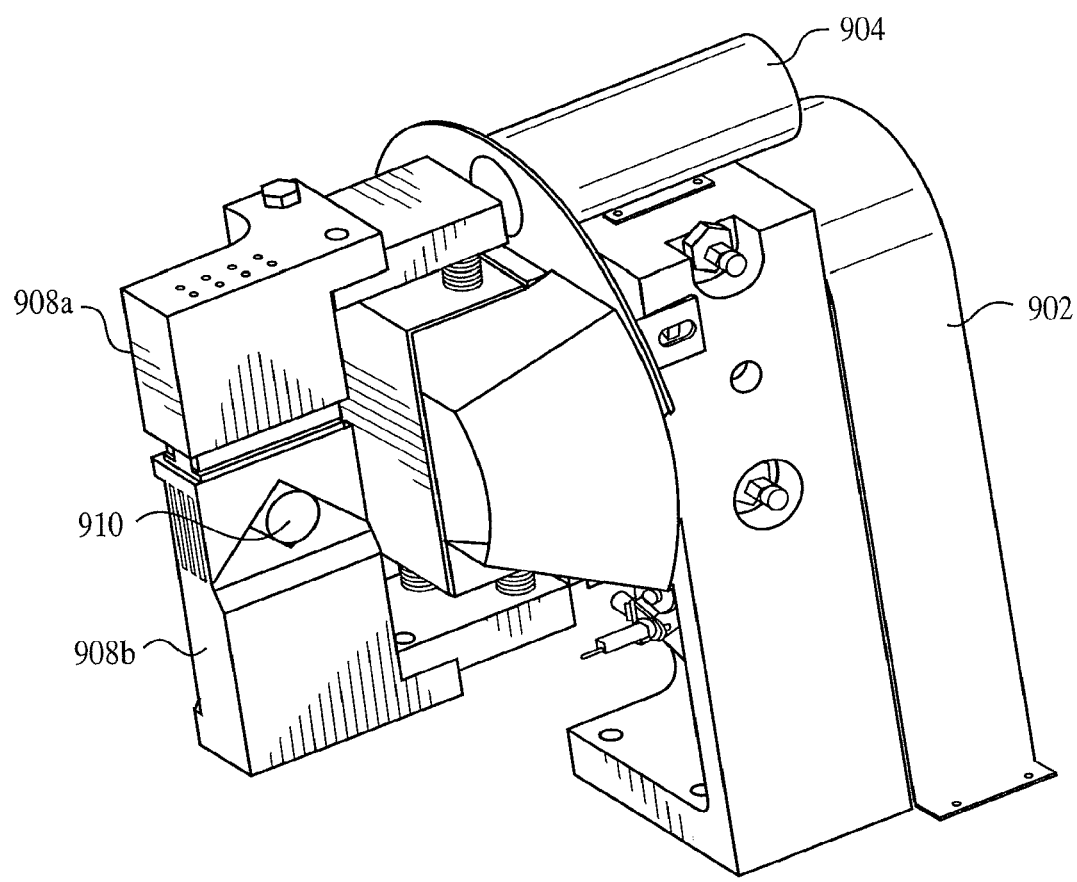
Figure 9E:
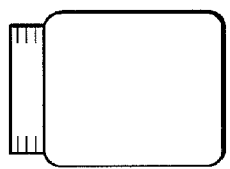
Figure 9F:
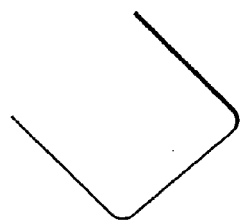
Figure 9G:
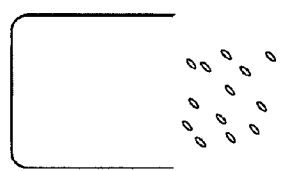

FIGS. 9e-9j show two bottle cutting and dispensing scenarios. In FIGS. 9e-9g, the top of the bottle is cut. In FIG. 9e, bottle 910 is placed upright in gripper assembly 901a, 901b. After the top portion of bottle 910 is cut, gripper assembly 901a, 901b begins to rotate bottle 910, as shown in FIG. 9e. After bottle 910 is rotated approximately 180°, as shown in FIG. 9f, the contents of bottle 910 can be emptied into a pill accumulation chute 1401a, 1401b. When the bottle is placed uptight in gripper assembly 901a, 901b, any cotton can be removed with the cutting operation. Cotton can also be removed, for example, by a the robot 801 vacuum.

Figure 9H:
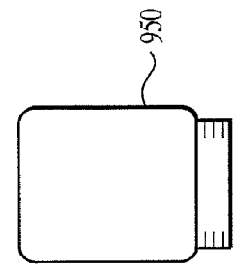
Figure 9I:
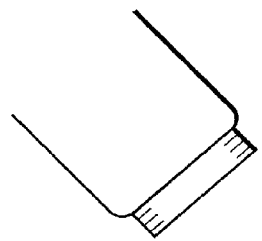
Figure 9J:
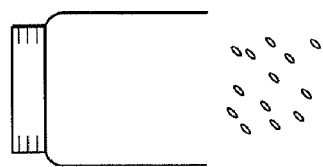
Figure 10:
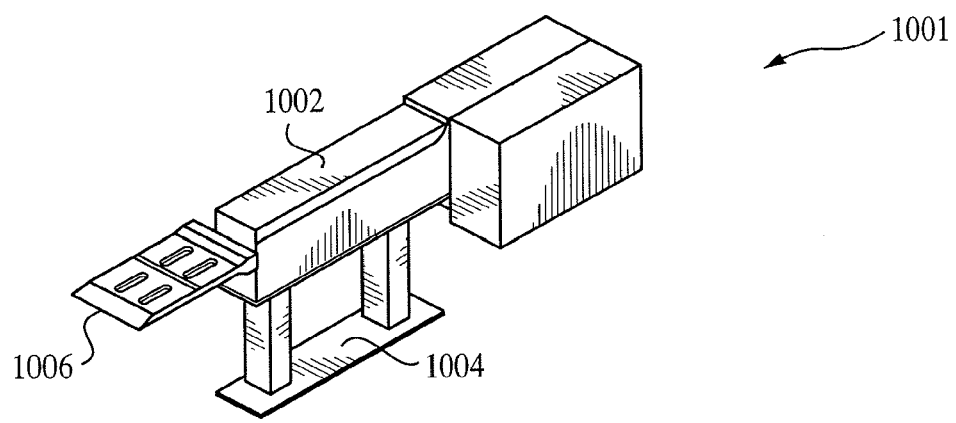
FIG. 10 is an exemplary embodiment of a cutter assembly of the ACES.

In FIGS. 9h-9j, the bottom of the bottle is cut. In FIG. 9h, bottle 910 is placed in gripper assembly 901a, 901b with the cap 950 facing down. After the bottom portion of bottle 910 is cut, gripper assembly 901a, 901b begins to rotate bottle 910, as shown in FIG. 9i. After bottle 910 is rotated approximately 180°, as shown in FIG. 9j, the contents of bottle 910 can be emptied into a pill accumulation chute 1401a, 1401b.

In an embodiment of the invention, a light beam can optionally be used to determine whether bottle 910 is held by grippers 908a, 908b. For example, control system 506 can optionally utilize a reflector 912 positioned, for example, on a side wall or portion of gripper 908b. In operation, reflector 912 will not detect light when grippers 908a, 908b holding a bottle 910. The light beam and reflector 812 can similarly be used to verify that bottle 910 is released from grippers 908a, 908b after the contents of bottle 910 have been emptied. That is, when reflector 812 detects light, grippers 908a, 908b are not holding a bottle 910.

Because some bottles 910 may contain residual glue from the literature that was removed from the bottle 910, a non-stick coating can optionally be added to grippers 908a, 908b to facilitate release of a bottle 910. In addition, a continuous stream or intermittent shot of air can optionally be used in addition to or in lieu of the non-stick coating to "blow" the bottle out of grippers 908a, 908b.

Robot 801 loads bottle 910 onto bottle platform 1204, preferably in a manner that accounts for the size and/or shape of the bottle(s) 910. For example, oblong and rectangular bottles may be oriented in a certain manner to allow grippers 908a, 908b to properly hold bottle 910. Robot 801 retracts and selects another bottle 910. Bottle platform 1204 also retracts, and the grippers 908a, 908b rotate (e.g., approximately 180°) the bottle 910 for cutting. A dust extraction sleeve 904 can optionally be utilized that draws the dust from the area while bottle 910 is cut.

Figure 11A:
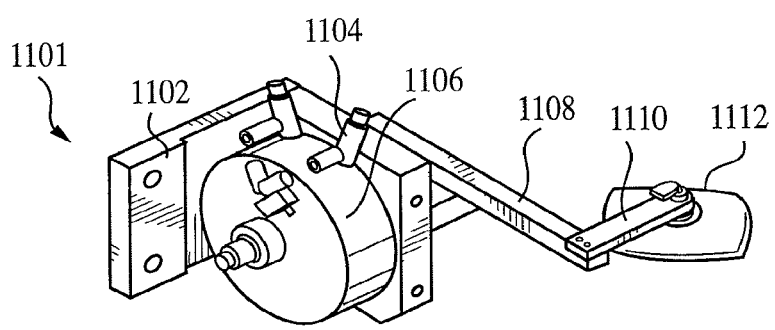
FIGS. 11a and 11b are various perspective views of an exemplary embodiment of a vacuum assembly of the ACBS.
Figure 11B:
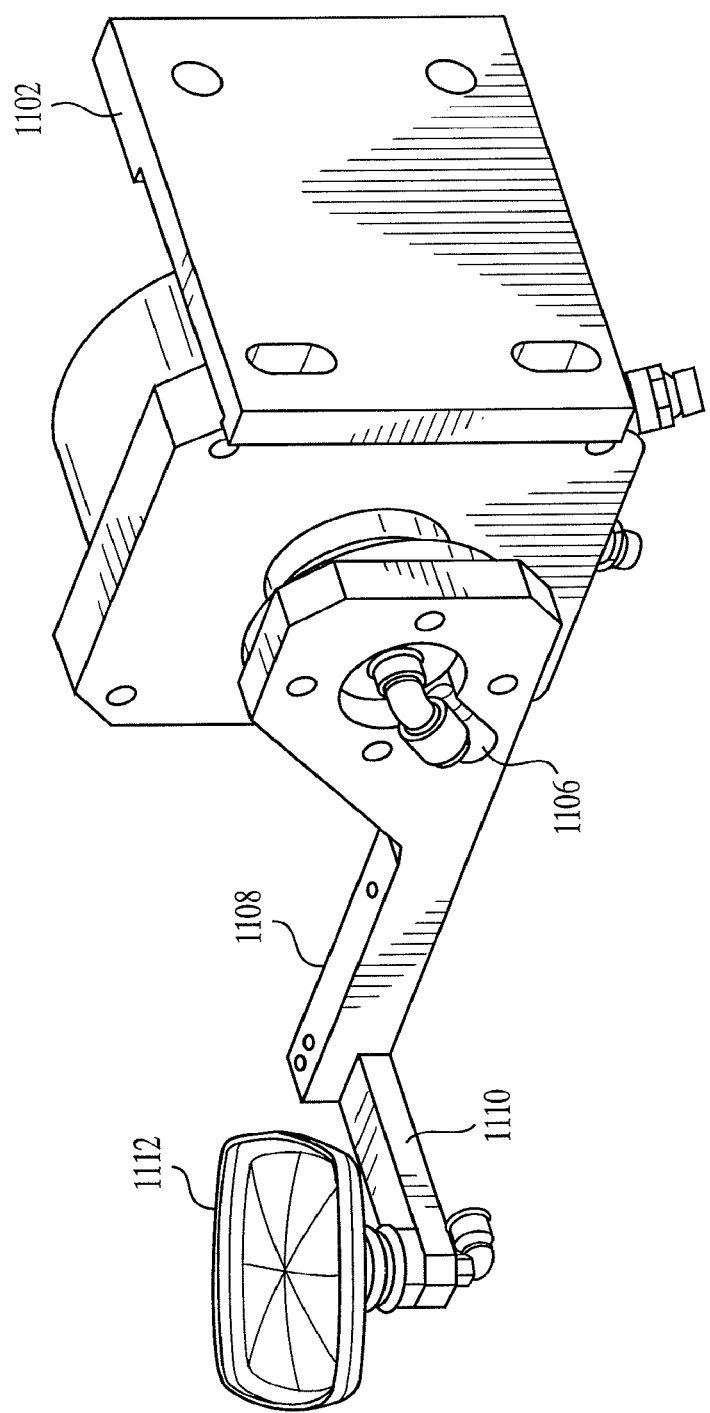
Figure 12A:
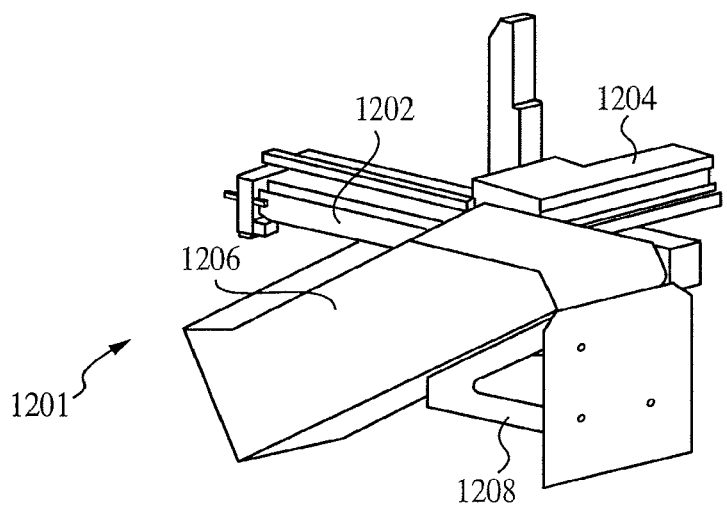
FIG. 12a is an exemplary embodiment of a bottle scrap chute of the ACBS.
Figure 12B:
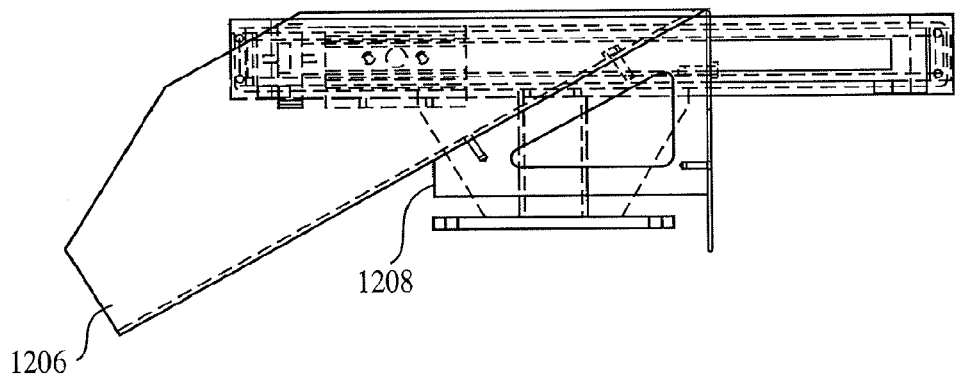
FIG. 12b is a side view of an exemplary embodiment of a bottle scrap chute of the ACBS in a first position.
Figure 12C:
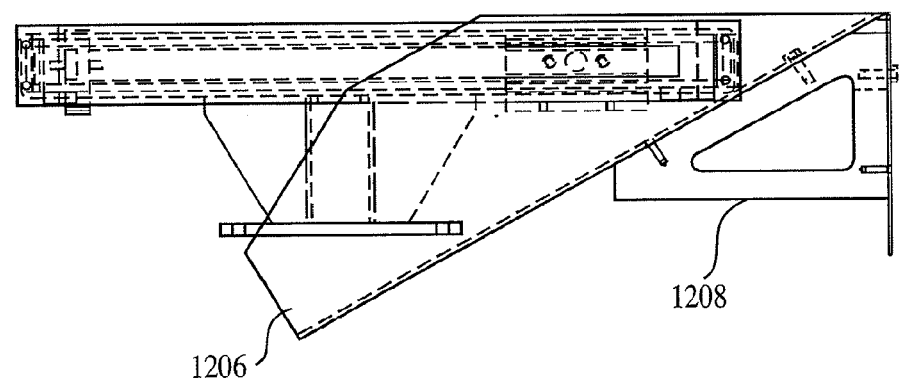
FIG. 12c is a side view of an exemplary embodiment of a bottle scrap chute of the ACES in a second position.
Figure 12D:
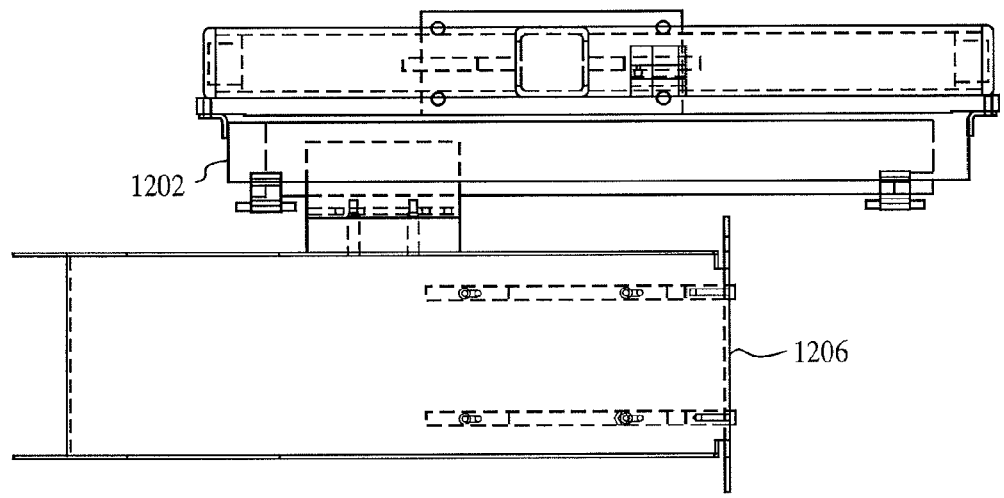
FIG. 12d is a top view of an exemplary embodiment of a bottle scrap chute of the ACBS in a first position.
Figure 12E:
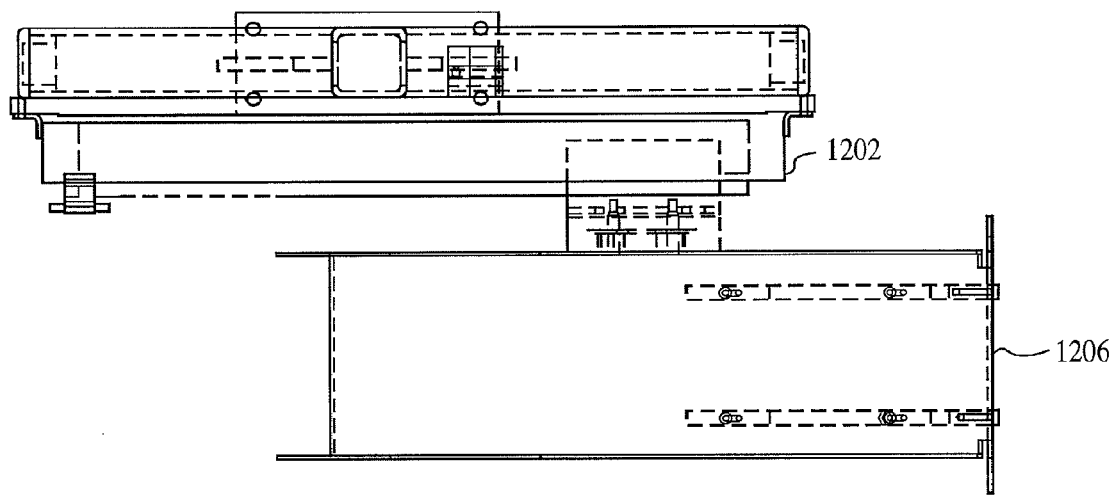
FIG. 12e is top view of an exemplary embodiment of a bottle scrap chute of the ACBS in a second position

FIGS. 11a and 11b show various views of an exemplary embodiment of a vacuum assembly 1101, which removes the cut portion of bottle 910 and places it into scrap chute 1201. In operation, rotary actuator 1106 is actuated to rotate rotary arm 1108 so that suction plate 1110 is rotated to (or near) the top of the cutting area (at or near, for example, the base of bottle 910). As cutter 1002 advances and blade 1006 cuts bottle 910, the cutting action raises the cut portion of bottle 910 to the suction cup 1110. Rotary actuator 1106 then rotates rotary arm 1108 so that bottle scrap 1112 can be placed into bottle scrap bin 1301. Grippers 908a, 908b then rotate bottle 910 so that the contents of bottle 910 are dumped into pill accumulation chute 1401, as illustrated in FIGS. 9e-9j. Vacuum assembly 1101 can also optionally comprise a mounting plate 1102 and/or a speed controller 1104 to control the speed of rotation of rotary arm 1108.

Figure 13:
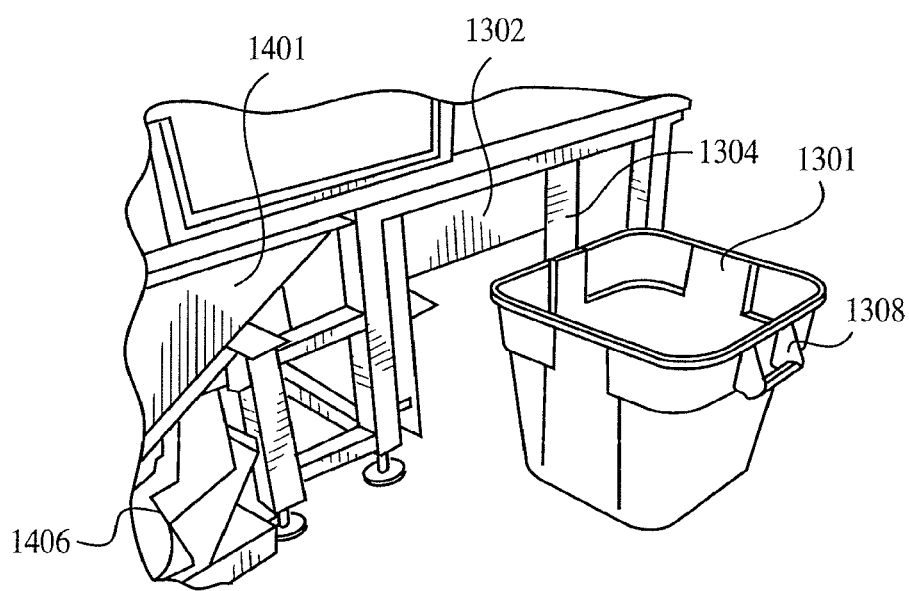
FIG. 13 is an exemplary embodiment of a bottle scrap bin of the ACBS.

FIG. 12 is an exemplary embodiment of scrap chute 1201a, 1201b which, after cutting, deflects the remaining portion of emptied bottles 910 and cut off bottle scraps 1112 into scrap bins 1301 (as shown, e.g., in FIG. 13). In an embodiment, once the contents of a bottle 910 have been emptied, chute 1206 (as shown, e.g., in FIG. 12) advances, as shown, for example, in FIGS. 12c and 12e. The advancement of chute 1206 can optionally be in a position that is substantially transverse with respect to conveyor belt 704 (as shown, e.g., in FIGS. 5 and 7). Grippers 908a, 908b release the remaining portion of bottle 910 onto chute 1206. Chute 1206 retracts, as shown for example in FIGS. 12b and 12d, and the remaining portion of bottle 1110 slides into scrap bin 1301 (FIG. 13). Chute 1206 also can optionally be used to deflect bottle scrap 1112 received from base vacuum assembly 1101 into scrap bin 1301.

Scrap chute 1201 can be mounted to, for example, a Festo rodless air cylinder 1202 (available from Festo Corporation, Hauppauge, N.Y.) which facilitates single axis movement. A vacuum hood (not shown) is preferably provided above each scrap bin 1301 to, for example, minimize pill dust contamination while changing the scrap bin trash bag. Vacuum capture velocities can be, for example, approximately 100 feet per minute. Scrap chute 1201 can also optionally comprise a support angle 1208 for mounting.

FIG. 13 shows scrap bin 1301 (positioned near accumulation chute 1401), preferably but optionally having a handle 1308 on each of any two opposing sides thereof. Sensors (not shown) can be utilized and positioned to monitor both scrap bin 1301 presence near scrap chute 1201 and high level conditions in scrap bin 1301.

In an embodiment of the present invention, a three-position selector switch (not shown) is optionally provided to divert the vacuum flow when changing either or both of scrap bins 1301a, 1301b. When the selector switch is set to OFF, the vacuum is diverted, for example, to the cutting area near cutters 1002a, 1002b (on both sides), and no vacuum is present at scrap bins 1301a, 1301b. When the selector switch is set to side 1, vacuum flow is diverted from the cutting/dumping area to scrap bin 1301a. Side 1 also optionally becomes disabled so that it does not cut any more bottles 910. The same operation preferably occurs at side 2 when the selector switch is set to side 2. A curtain 1302 is optionally provided to help isolate any dust inside bin housing area 1304.

Figure 14:
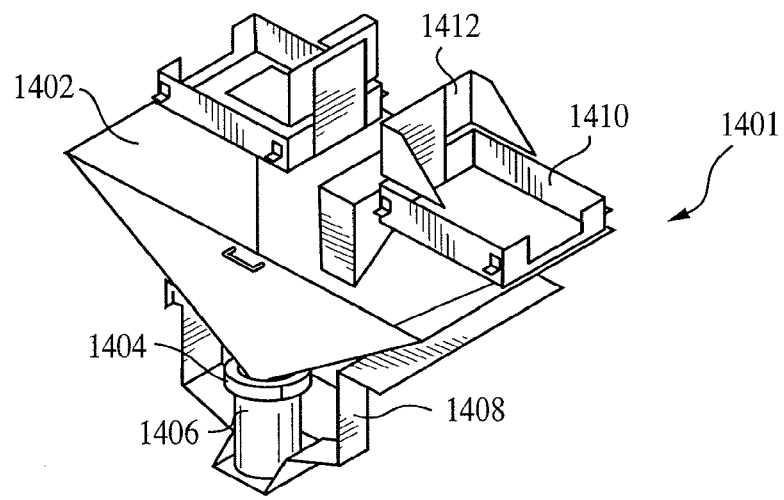
FIG. 14 is an exemplary embodiment of a pill accumulation chute of the ACBS.

FIG. 14 is an exemplary embodiment of a pill accumulation chute 1401. The contents of bottle 910 (e.g., pills) are emptied into funnel 1402 that directs the pills into bulk-up container 1406. Manifold 1404 connects bulk-up container 1406 to funnel 1402, and can optionally include a vacuum to absorb any pill dust that may emanate from placing the pills in bulk-up container 1406. Vacuum capture velocities can be, for example, approximately 20 feet per minute. A support bar 1408 can also optionally be provided. Top chute 1410 and deflector 1412 can also optionally be provided to guide bottle 910 contents.

Figure 15:
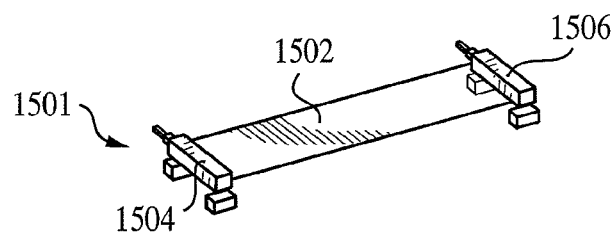
FIG. 15 is an exemplary embodiment of an scanning light beam of the ACBS.

Referring to FIG. 15, a light beam unit (e.g., a Banner A-Gage™ Mini-Array™ unit) 1501 is shown that can be positioned, for example, on opposing sides of accumulation chute 1401 to verify that product did indeed empty out of bottle 910 and onto pill collection chute 1401. Light beam unit 1501 is preferably but optionally integrated with control system 506. Light beam units 1501 can include a light emitter 1406 and receiver 1404. Light emitter 1406 sends, for example, a series of light beams to receiver 1404. As bottle 910 product falls onto accumulation chute 1401, it breaks the light beam, thus providing a signal indicating that product is still being dispensed. As bottle 910 product stops falling onto accumulation chute 1401, the light beam is unbroken, thereby providing a signal indicating that product is not being dispensed.

Figure 16:
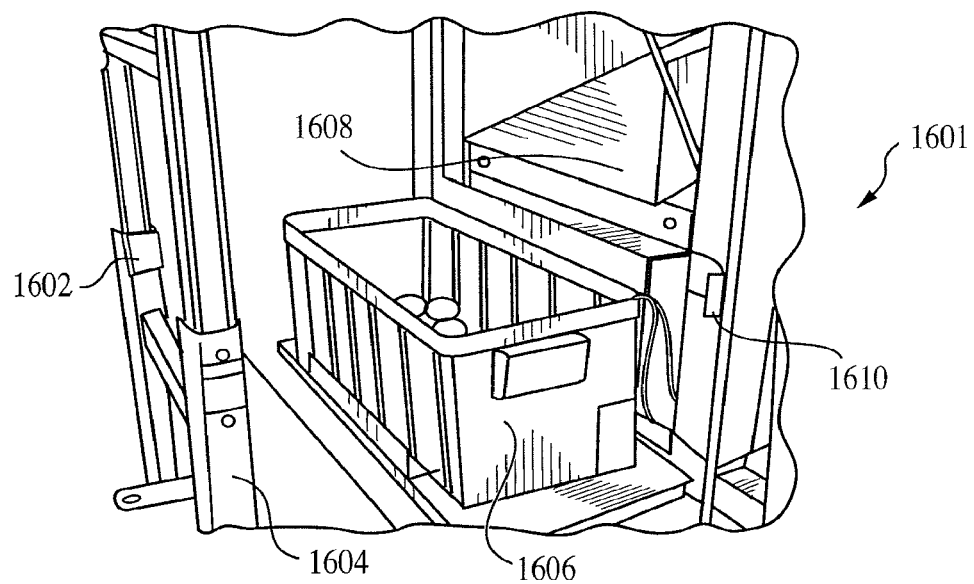
FIG. 16 is an exemplary embodiment of a bottle return bin of the ACBS.

FIG. 16 is an exemplary embodiment of a bottle return bin 1601. Bottle return bin 1601 receives unopened manufacturer bottles that were not picked by robot 801. Any bottles 910 that, for example, are not recognized by vision system 518 (e.g., wrong bottle, fallen over) are driven off conveyor belt 702 and onto bottle return chute 514, which transports bottles 910 into bottle return bin 1601. A retroreflective sensor, for example, can optionally be utilized to detect that the bin 1601 is both full and present.

Figure 17:
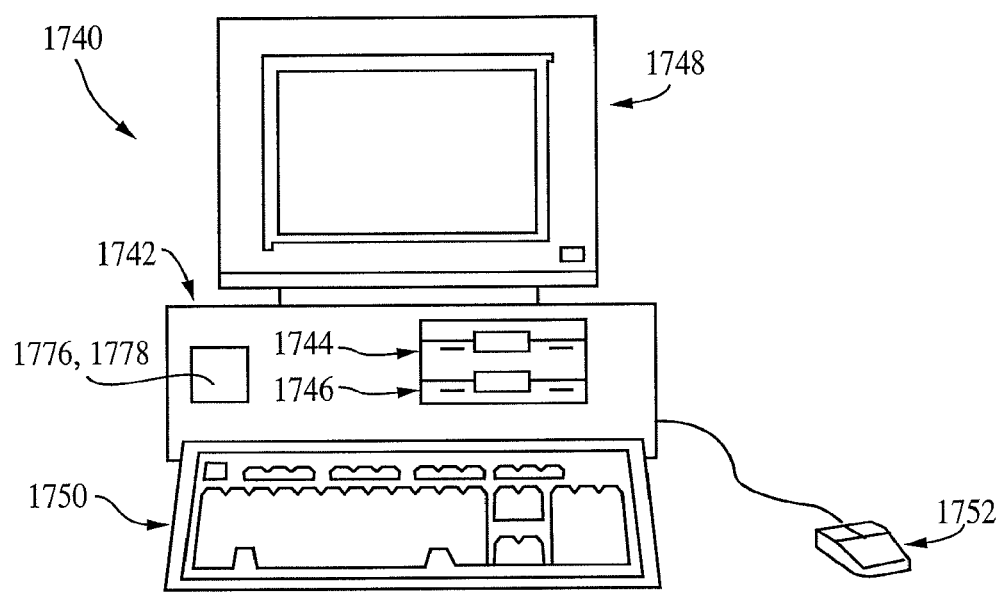
FIG. 17 illustrates a computer that can be used in implementing embodiments of the present invention.

Viewed externally in FIG. 17, a computer system (e.g., the host computer 201 or the local computers) designated by reference numeral 1740 has a computer 1742 having disk drives 1744 and 1746. Disk drive indications 1744 and 1746 are merely symbolic of a number of disk drives which might be accommodated by the computer system. Typically, these would include a floppy disk drive 1744, a hard disk drive (not shown externally) and a CD ROM indicated by slot 1746. The number and type of drives vary, typically with different computer configurations. Disk drives 1744 and 1746 are in fact optional, and for space considerations, are easily omitted from the computer system used in conjunction with the production process/apparatus described herein.

The computer system also has an optional display 1718 upon which information screens may be displayed. In some situations, a keyboard 1750 and a mouse 1752 are provided as input devices through which a user's actions may be inputted, thus allowing input to interface with the central processing unit 1742. Then again, for enhanced portability, the keyboard 1750 is either a limited function keyboard or omitted in its entirety. In addition, mouse 1752 optionally is a touch pad control device, or a track ball device, or even omitted in its entirety as well, and similarly may be used to input a user's selections. In addition, the computer system also optionally includes at least one infrared transmitter and/or infrared received for either transmitting and/or receiving infrared signals, as described below.

Figure 18:
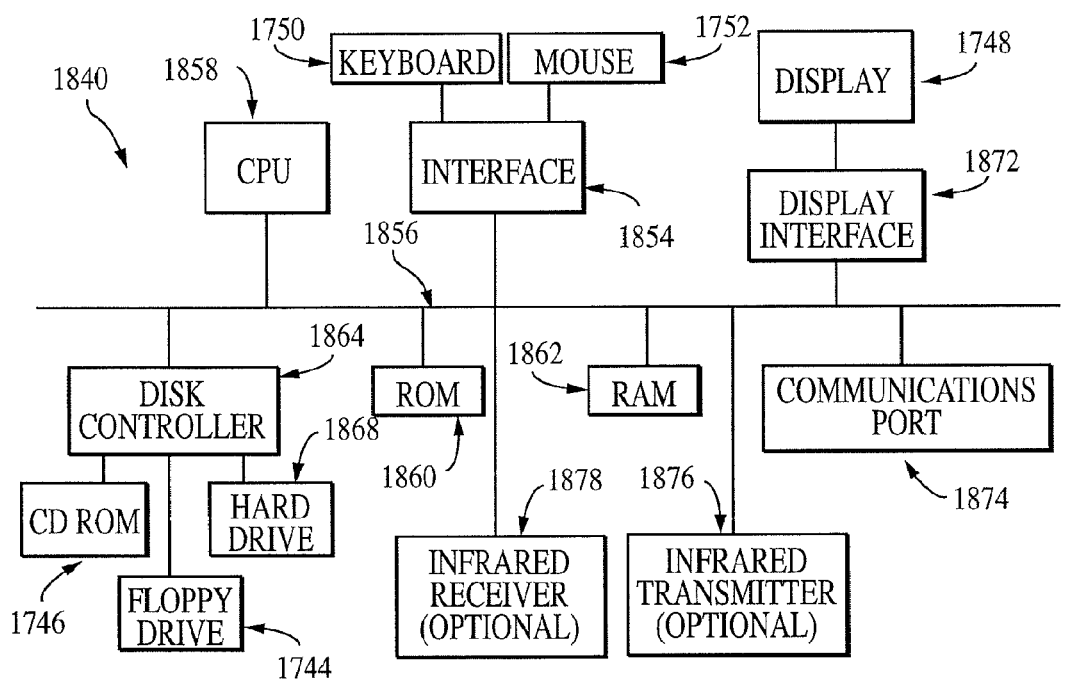
FIG. 18 is a block diagram of internal hardware of the example computer/control system shown in FIG. 5.

FIG. 18 illustrates a block diagram of one example of the internal hardware 1840 configured to perform various example steps as described above. A bus 1856 serves as the main information highway interconnecting various components therein. CPU 1858 is the central processing unit of the internal hardware 1840, performing calculations and logic operations required to execute the control/operation processes of the present invention as well as other programs. Read only memory (ROM) 1860 and random access memory (RAM) 1862 constitute the main memory of the internal hardware 1840. Disk controller 1864 interfaces one or more disk drives to the system bus 1856. These disk drives are, for example, floppy disk drives 1744, or CD ROM or DVD (digital video disks) drives 1746, or internal or external hard drives 1868. These various disk drives and disk controllers are optional devices.

A display interface 1872 interfaces display 1748 and permits information from the bus 1856 to be displayed on display 1748. Communications with external devices such as the other components (e.g., a PLC) of the system described above, occur utilizing, for example, communication port 1874. Optical fibers and/or electrical cables and/or conductors and/or optical communication (e.g., infrared, and the like) and/or wireless communication (e.g., radio frequency (RF), and the like) can be used as the transport medium between the external devices and communication port 1874. Peripheral interface 1854 interfaces the keyboard 1750 and mouse 1752, permitting input data to be transmitted to bus 1856. In addition to these components, the internal hardware 1840 also optionally include an infrared transmitter and/or infrared receiver. Infrared transmitters are optionally utilized when the computer system is used in conjunction with one or more of the processing components/stations/modules that transmits/receives data via infrared signal transmission. Instead of utilizing an infrared transmitter or infrared receiver, the computer system may also optionally use a low power radio transmitter 1876 and/or a low power radio receiver 1878. The low power radio transmitter transmits the signal for reception by components of the production process, and receives signals from the components via the low power radio receiver. The low power radio transmitter and/or receiver are standard devices in industry.

Although the server in FIG. 18 is illustrated having a single processor 1858, a single hard disk drive 1868 and a single local memory 1862, the internal hardware 1840 is optionally suitably equipped with any multitude or combination of processors or storage devices. For example, the computer 1742 may be replaced by, or combined with, any suitable processing system operative in accordance with the principles of embodiments of the present invention, including sophisticated calculators, and hand-held, laptop/notebook, mini, mainframe and super computers, as well as processing system network combinations of the same.

Figure 19:
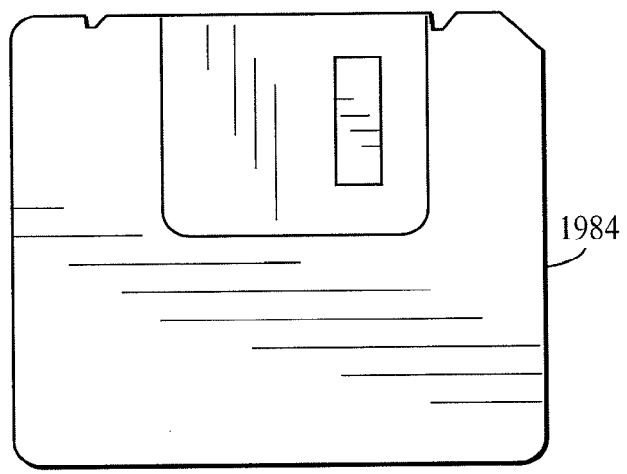
FIG. 19 illustrates one example of a memory medium which may be used for storing computer programs of embodiments of the present invention.

FIG. 19 is, an illustration of an example computer readable memory medium 1984 utilizable for storing computer readable code or instructions. As one example; medium 1984 may be used with disk drives illustrated in FIG. 18. Typically, memory media such as floppy disks, or a CD ROM, or a digital video disk will contain, for example, a multi-byte locale for a single byte language and the program information for controlling system 410 and/or 450 to enable, for example, control system 506 to perform the functions described herein. Alternatively, ROM 1860 and/or RAM 1862 illustrated in FIG. 18 can also be used to store the program information that is used to instruct CPU 1858 to perform the operations associated with various automated processes of the present invention. Other examples of suitable computer readable media for storing information include magnetic, electronic, or optical (including holographic) storage, some combination thereof, etc.

Figure 20:
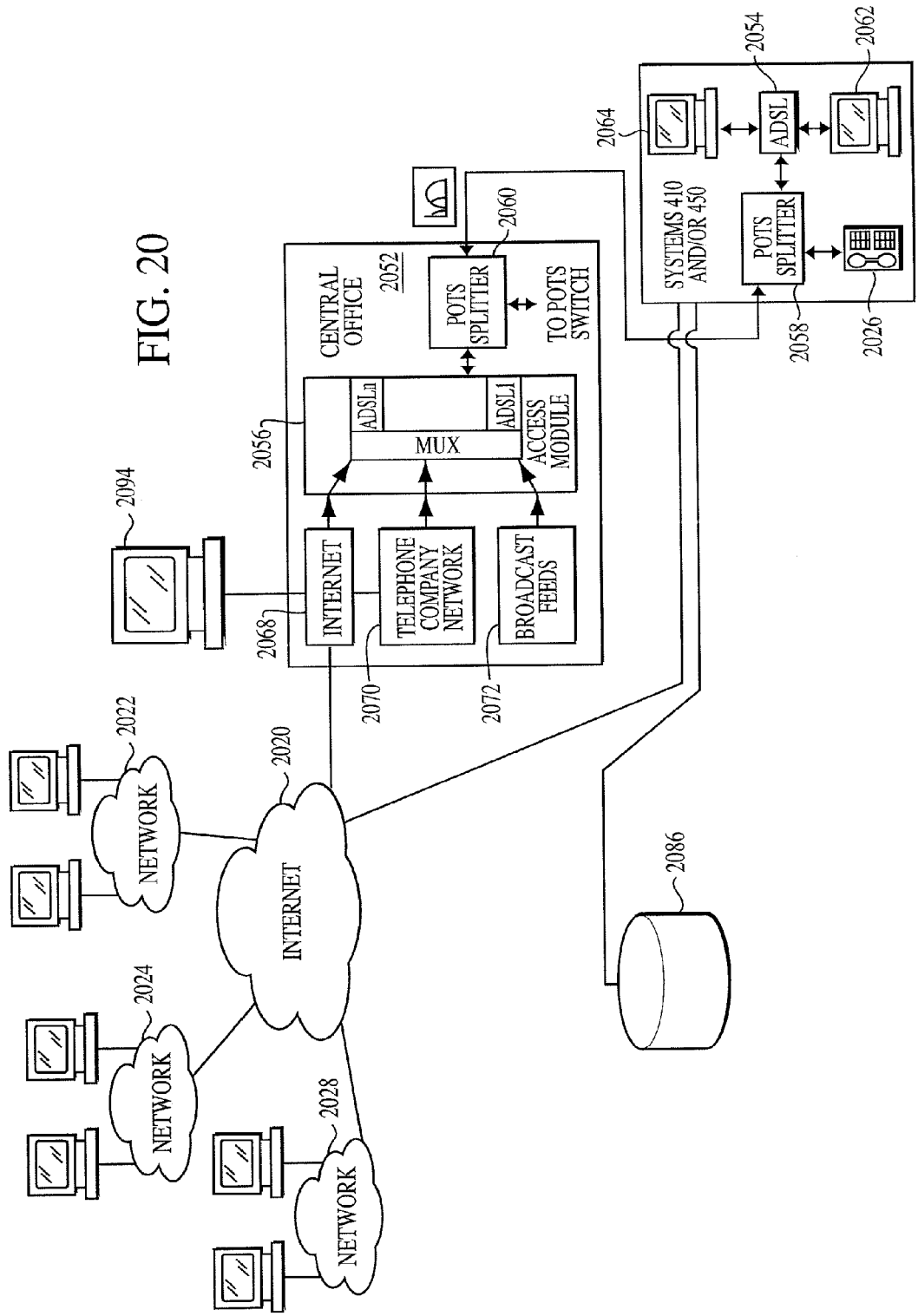
FIG. 20 is a block diagram representation of an example embodiment of computer network(s) implementing embodiments of the present invention.

FIG. 20 is an illustration of the architecture of the combined Internet, POTS (plain, old, telephone service), and ADSL (asymmetric, digital, subscriber line) for use in accordance with the principles of the present invention. In other words, instead of using dedicated lines and such communication schemes associated with, for example, control system 506, this example embodiment envisions a remotely controllable system. Furthermore, it is to be understood that the use of the Internet, ADSL, and POTS are for exemplary reasons only and that any suitable communications network may be substituted without departing from the principles of the present invention. This particular example is briefly discussed below.

In FIG. 20, to preserve POTS and to prevent a fault in the ADSL equipment 2054, 2056 from compromising analog voice traffic 2026 the voice part of the spectrum (the lowest 4 kHz) is separated from the rest by a passive filter, called a POTS splitter 2058, 2060. The rest of the available bandwidth—from about 10 kHz to 1 MHz—carries data at, for example, rates up to 6 bits per second for every hertz of bandwidth from data equipment 2062, 2064, and 2094. The ADSL equipment 2056 then has access to a number of destinations including, for example, the Internet 2020 or other data communications networks, and other destinations 2070.

To exploit the higher frequencies, ADSL makes use of advanced modulation techniques, of which the best known is the discrete multitone (DMT) technology. As its name implies, ADSL transmits data asymmetrically—at different rates upstream toward the central office 2052 and downstream toward systems 410 and/or 450.

Cable modems come in many forms. Most create a downstream data stream out of one of the 6-MHz TV channels that occupy spectrum above 50 MHz (and more likely 550 MHz) and carve an, upstream channel out of the 5-50-MHz band, which is currently unused. Using 64-state quadrature amplitude modulation (64 QAM), a downstream channel can realistically transmit about 30 Mb/s (the oft-quoted lower speed of 10 Mb/s refers to PC rates associated with Ethernet connections). Upstream rates differ considerably from vendor to vendor, but good hybrid fiber/coax systems can deliver upstream speeds of a few megabits per second. Thus, like ADSL, cable modems transmit much more information downstream than upstream. Then Internet architecture 2020 and ADSL architecture 2054, 2056 may also be combined with, for example, other networks 2022, 2024, and 2028.

In accordance with the principles of the present invention, in one example, a main computing server (e.g., in one embodiment, control system 506) implementing the process of the invention may be located on one or more computing nodes or terminals (e.g., on networks 2022, 2024 and/or 2028. Then, various users (e.g., one or more of the local computers described above) may interface with the main server via, for instance, the ADSL equipment discussed above, and access the information and processes of the present invention from remotely located PCs. Database 2086 is accessible via, for example, control system 506.

In general, it should be emphasized that the various components of embodiments of the present invention can be implemented in hardware, software or a combination thereof. In such embodiments, the various components and steps would be implemented in hardware and/or software to perform the functions of embodiments of the present invention. Any presently available or future developed computer software language and/or hardware components can be employed in such embodiments of the present invention. For example, at least some of the functionality mentioned above could be implemented using Visual Basic, C, C++, or any assembly language appropriate in view of the processor(s) being used. It could also be written in an interpretive environment such as Java and transported to multiple destinations to various users.

The many features and advantages of embodiments of the present invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method comprising:
    holding a pharmaceutical container with a gripper unit;
    determining an orientation of the pharmaceutical container;
    orientating the pharmaceutical container responsive to the determined orientation, wherein the cutting of the pharmaceutical container is performed in response to orientation of the pharmaceutical container;
    cutting the pharmaceutical container with a cutter; and
    rotating the pharmaceutical container with a rotating unit operable with the gripper unit to empty contents of the pharmaceutical container into a bulk container after the pharmaceutical container is cut.

2. The method of claim 1, further comprising:
    rotating the pharmaceutical container to a first position to receive a cut portion of the pharmaceutical container, and
    rotating to a second position to place the cut portion in a waste repository.

3. The method of claim 2, further comprising:
    utilizing a vacuum to retain the cut portion of the pharmaceutical container when the rotating unit is in the first position, and decreasing the vacuum when the rotating unit is in the second position to effect release of the cut portion.

4. The method of claim 1, further comprising:
    receiving a portion of the pharmaceutical container subsequent to emptying the contents of the pharmaceutical container using a scrap chute.

5. The method of claim 4, further comprising:
    moving to a proximal position with respect to the gripper unit to receive a portion of the pharmaceutical container held by the gripper unit subsequent to emptying the contents of the pharmaceutical container when the scrap chute is in a distal position with respect to the gripper unit prior to emptying the contents of the pharmaceutical container, and
    returning the scrap chute to the distal position to place the portion of the pharmaceutical container held by the gripper unit in a scrap bin.

6. The method of claim 1, further comprising:
    determining when the contents are no longer being emptied directly from the pharmaceutical container using a sensor unit.

7. The method of claim 6, further comprising:
    detecting when the pharmaceutical container is no longer being held by said gripper unit using a detection system.

8. The method of claim 7, further comprising:
    detecting when the pharmaceutical container is being held by the gripper unit when light from a light beam source is not reflected.

9. The method of claim 8, further comprising:
    determining whether pharmaceuticals are authorized by a control unit when indicia associated with the pharmaceutical container is read by an indicia reader.

10. The method of claim 1, further comprising:
    receiving identification information of a system operator by a control unit.

11. The method of claim 1, further comprising:
    verifying that the pharmaceutical container is the correct diameter, has the correct overhead shape, or both is the correct diameter and has the correct overhead shape using a vision unit.

12. The method of claim 1, further comprising:
    placing the pharmaceutical container in the gripper unit, and
    removing cotton with at least a cutting operation, a robot vacuum, or both a cutting operation and a robot vacuum.

13. The method of claim 1, further comprising:
    verifying that the contents emptied directly from the pharmaceutical container using a light beam unit.

14. The method of claim 1, further comprising:
    viewing the pharmaceutical container using an electronic viewer before holding and cutting the pharmaceutical container for providing positioning information of the pharmaceutical container.

15. The method of claim 1, further comprising:
providing a vacuum flow in the area of the cutter.

16. The method of claim 1, further comprising:
transporting the pharmaceutical container;
determining information provided on the pharmaceutical container to identify the pharmaceuticals contained therein; and
determining whether the pharmaceuticals are authorized to be emptied from the pharmaceutical container into a bulk container responsive to the determined information,
wherein the pharmaceutical container is held with the gripper unit when a determination is made that the pharmaceuticals are authorized to be emptied.

17. The method of claim 1, wherein cutting pharmaceutical container comprises:
cutting the pharmaceutical container on a sidewall of the of the pharmaceutical container, a bottom of the pharmaceutical container, or both the sidewall and the bottom of the pharmaceutical container.

18. The method of claim 1, further comprising:
determining when the contents of the pharmaceutical container are no longer being emptied into the bulk container;
controlling cutting and rotating of the pharmaceutical container to empty the contents into the bulk container; and
periodically emptying bulk container contents of the bulk container into an automated pharmaceutical dispensing system for subsequent automated dispensing of the pharmaceutical in into an additional pharmaceutical container responsive to a patient specific prescription order.

19. A method comprising:
holding a pharmaceutical container with a gripper unit;
transporting the pharmaceutical container;
determining information provided on the pharmaceutical container to identify pharmaceuticals contained within the pharmaceutical container; and
determining whether the pharmaceuticals are authorized to be emptied from the pharmaceutical container into a bulk container responsive to the determined information, wherein the pharmaceutical container is held with the gripper unit when a determination is made that the pharmaceuticals are authorized to be emptied;
cutting the pharmaceutical container with a cutter; and
rotating the pharmaceutical container with a rotating unit operable with the gripper unit to empty contents of the pharmaceutical container into a bulk container after the pharmaceutical container is cut.

\* \* \* \* \*